(12) United States Patent
Chauhan et al.

(10) Patent No.: US 11,925,467 B2
(45) Date of Patent: Mar. 12, 2024

(54) SYSTEM AND METHOD FOR ASSESSING QRS COMPONENTS AND LIKELIHOOD OF RESPONSE TO CARDIAC RESYNCHRONIZATION THERAPY

(71) Applicant: University Health Network, Toronto (CA)

(72) Inventors: Vijay Singh Chauhan, Toronto (CA); Adrian Michael Suszko, Toronto (CA)

(73) Assignee: University Health Network, Toronto (CA)

( * ) Notice: Subject to any disclaimer, the term of this patent is extended or adjusted under 35 U.S.C. 154(b) by 159 days.

(21) Appl. No.: 17/052,247

(22) PCT Filed: Apr. 30, 2019

(86) PCT No.: PCT/CA2019/050563
§ 371 (c)(1),
(2) Date: Nov. 2, 2020

(87) PCT Pub. No.: WO2019/210410
PCT Pub. Date: Nov. 7, 2019

(65) Prior Publication Data
US 2021/0169393 A1 Jun. 10, 2021

Related U.S. Application Data

(60) Provisional application No. 62/666,766, filed on May 4, 2018.

(51) Int. Cl.
*A61B 5/30* (2021.01)
*A61B 5/00* (2006.01)
(Continued)

(52) U.S. Cl.
CPC .............. *A61B 5/352* (2021.01); *A61B 5/30* (2021.01); *A61B 5/35* (2021.01); *A61B 5/4836* (2013.01);
(Continued)

(58) Field of Classification Search
CPC ..................................................... A61B 5/352
(Continued)

(56) References Cited

U.S. PATENT DOCUMENTS

| 4,073,011 A | 2/1978 | Cherry et al. |
| 5,341,811 A | 8/1994 | Cano |

(Continued)

FOREIGN PATENT DOCUMENTS

| CA | 2253760 A1 | 11/1997 | |
| WO | WO-2016183683 A1 * | 11/2016 | ........... A61B 5/0006 |

OTHER PUBLICATIONS

Bayés De Luna et al., "Ambulatory sudden cardiac death: Mechanisms of production of fatal arrhythmia on the basis of date from 157 cases", Am Heart Journal, Jan. 1989, 117(1): 151-159.
(Continued)

*Primary Examiner* — Nicole F Lavert

(57) ABSTRACT

Various embodiments are described herein for a system and a method for assessing a risk of ventricular arrhythmias for a patient. For example, the method may comprise receiving ECG data obtained from the patient; analyzing the ECG data to detect abnormal QRS peaks; determining the risk of ventricular arrhythmias for the patient based on the detected abnormal QRS peaks; and providing an indication of the risk of ventricular arrhythmias for the patient. The system may be configured to perform this method.

20 Claims, 12 Drawing Sheets

(51) Int. Cl.
   *A61B 5/35* (2021.01)
   *A61B 5/352* (2021.01)
   *A61N 1/362* (2006.01)

(52) U.S. Cl.
   CPC ............ *A61B 5/4848* (2013.01); *A61N 1/362* (2013.01); *A61B 2562/222* (2013.01)

(58) Field of Classification Search
   USPC ...................................................... 600/510
   See application file for complete search history.

(56) References Cited

U.S. PATENT DOCUMENTS

| | | | |
|---|---|---|---|
| 5,609,158 | A | 3/1997 | Chan |
| 5,891,047 | A | 4/1999 | Lander et al. |
| 6,512,945 | B1 | 1/2003 | Houim et al. |
| 7,142,907 | B2 | 11/2006 | Xue et al. |
| 7,912,544 | B1 | 3/2011 | Min et al. |
| 8,285,371 | B2 | 10/2012 | Li et al. |
| 8,437,839 | B2 | 5/2013 | Lux |
| 2002/0143264 | A1 | 10/2002 | Ding et al. |
| 2011/0111525 | A1 | 5/2011 | Struck et al. |
| 2011/0319954 | A1 | 12/2011 | Niazi et al. |
| 2012/0197148 | A1 | 8/2012 | Levitan et al. |
| 2013/0123653 | A1* | 5/2013 | Maskara ................ A61B 5/746 600/516 |
| 2016/0081573 | A1 | 3/2016 | Niebauer et al. |
| 2017/0368360 | A1* | 12/2017 | Hahn ..................... A61N 1/365 |
| 2018/0125385 | A1* | 5/2018 | Chauhan ................ A61B 5/366 |

OTHER PUBLICATIONS

Hauser et al., "Lessons From the Failure and Recall of an Implantable Cardioverter-Defibrillator", Circ., 2005; 112: 2040-2042.
Kuchar et al., Prediction of Serious Arrhythmic Events After Myocardial Infarction: Signal-Averaged Electrocardiogram Holter Monitoring and Radionuclide Ventriculography, JACC, 1987, 9(3): 531-538.
Rosengarten et al., "Can QRS scoring predict left ventricular scar and clinical outcomes?", EP Europace, 2013, 15(7): 1034-41.
Brenyo et al., "QRS Fragmentation and the Risk of Sudden Cardiac Death in MADIT M", J. Cardiovasc Electrophysiol., 2012, 23(12): 1343-48.
Cain et al., "Signal-averaged electrocardiography," Journal of the American College of Cardiology, 1996, 27(1): 238-249.
Cvijić et al., "Time Course of Electrical Remodeling of Native Conduction After Cardiac Resynchronization Therapy and Its Impact on Clinical Outcome", J. Card. Fail., 2017 (Epub 2016), 23(3): 257-261.
Morita et al., "Fragmented QRS as a marker of conduction abnormality and a predictor of prognosis of Brugada syndrome", Circulation, 2008, 118(17): 1697-704.
Bilchick et al., "Impact of mechanical activation, scar and electrical timing on cardiac resynchronization therapy response and clinical outcomes", J. Am. Coll. Cardiol., 2014, 63(16): 1657-1666.
Final Office Action and Notice of References Cited dated Apr. 29, 2021 in U.S. Appl. No. 15/575,527 (12 pages).
Non-final Office Action and Notice of References Cited dated Sep. 21, 2020 in U.S. Appl. No. 15/575,527 (13 pages).
International Search Report and Written Opinion dated Jul. 4, 2019 in International Patent Application No. PCT/CA2019/050563 (8 pages).
Sapp et al., "Cardiac Resynchronization Therapy Reduces Ventricular Arrhythmias in Primary but Not Secondary Prophylactic Implantable Cardioverter Defibrillator Patients: Insight From the Resynchronization in Ambulatory Heart Failure Trial", Arrhythmia and Electrophysiology, Mar. 1, 2017, 10(3): e004875 (pp. 1-9).
Al Hebaishi et al., "Predictors of Cardiac Resynchronization Therapy Response: The Pivotal Role of Electrocardiogram", The Scientific World Journal, Mar. 20, 2013, 2013: 837086 (pp. 1-6).
Rickard et al., "QRS fragmentation is not associated with poor response to cardiac resynchronization therapy", Ann Noninvasive Electrocardiol., 2011, 16(2): 165-171.
Celikyurt et al., "Relationship between fragmented QRS and response to cardiac resynchronization therapy", J Interv Card Electrophysiol., 2012; 35(3):337-42.
Russo et al., "ACCF/HRS/AHA/ASE/HFSA/SCAI/SCCT/SCMR 2013 appropriate use criteria for implantable cardioverter-defibrillators and cardiac resynchronization therapy: a report of the American College of Cardiology Foundation appropriate use criteria task force", Heart Rhythm Society et al., J Am Coll Cardiol., 2013, 61(12):1318-1368.
Leyva et al., "20 years of cardiac resynchronization therapy", J. Am. Coll. Cardiol., 2014, 64(10):1047-1058.
Khan et al., "Targeted left ventricular lead placement to guide cardiac resynchronization therapy: the TARGET study: a randomized, controlled trial", J. Am. Coll. Cardiol., 2012, 59(17):1509-1518.
Gold et al., "The relationship between ventricular electrical delay and left ventricular remodelling with cardiac resynchronization therapy", Eur Heart J., 2011, 32(20):2516-2524.
Auricchio et al., "Characterization of left ventricular activation in patients with heart failure and left bundle-branch block", Circulation, 2004, 109(9):1133-1139.
Auricchio et al., "Does Cardiac Resynchronization Therapy Benefit Patients With Right Bundle Branch Block: Cardiac Resynchronization Therapy Has a Role in Patients With Right Bundle Branch Block", Circ Arrhythm Electrophysiol., 2014, 7(3):532-542.
Flowers et al., "The anatomic basis for high-frequency components in the electrocardiogram", Circulation, 1969, 39(4): 531-539.
Igarashi et al., "Fragmented QRS Is a Novel Risk Factor for Ventricular Arrhythmic Events After Receiving Cardiac Resynchronization Therapy in Nonischemic Cardiomyopathy", J Cardiovasc Electrophysiol., 2017, 28(3):327-335.
Sinha et al., "Fragmented QRS as a Marker of Electrical Dyssynchrony to Predict Inter-Ventricular Conduction Defect by Subsequent Echocardiographic Assessment in Symptomatic Patients of Non-Ischemic Dilated Cardiomyopathy", Cardiology Res., 2016; 7(4): 140-145.
Tigen et al., "The utility of fragmented QRS complexes to predict significant intraventricular dyssynchrony in nonischemic dilated cardiomyopathy patients with a narrow QRS interval", Can. J. Cardiol., 2009, 25(9): 517-522.
Birnie et al., "Impact of QRS morphology and duration on outcomes after cardiac resynchronization therapy: Results from the Resynchronization-Defibrillation for Ambulatory Heart Failure Trial (RAFT)", Circulation Heart Fail, 2013; 6(6): 1190-1198.
Hawkins et al., "Selecting patients for cardiac resynchronization therapy: electrical or mechanical dyssynchrony?", Eur Heart J., 2006, 27(11): 1270-1281.
Das et al., "Fragmented QRS on twelve-lead electrocardiogram predicts arrhythmic events in patients with ischemic and nonischemic cardiomyopathy", Heart Rhythm, 2010 (Epub 2009), 7(1): 74-80.
Cintron et al., "Prognostic significance of serial changes in left ventricular ejection fraction in patients with congestive heart failure", The V-HeFT VA Cooperative Studies Group, Circulation, 1993; 87(6 Suppl): VI17-23.
Bleeker et al., "Clinical versus echocardiographic parameters to assess response to cardiac resynchronization therapy", Am J Cardiol., 2006; 97(2):260-3.
Rickard et al., "Left Ventricular Size does not Modify the Effect of QRS Duration in Predicting Response to Cardiac Resynchronization Therapy", Pacing Clin. Electrophysiol., 2017, 40(5):482-487.
Kosinski et al., "A weighted generalized score statistic for comparison of predictive values of diagnostic tests", Stat Med., 2013 (Epub 2012), 32(6):964-77.
Karaca et al., "Native Electrocardiographic QRS Duration after Cardiac Resynchronization Therapy: The Impact on Clinical Outcomes and Prognosis", J. Card. Fail., 2016, 22(10):772-80.
Sebag et al., "Reverse electrical remodeling by cardiac resynchronization therapy: prevalence and clinical impact", J Cardiovasc Electrophysiol., 2012; 23:1219-27.

(56) References Cited

OTHER PUBLICATIONS

Dizon et al., "Loss of left bundle branch block following biventricular pacing therapy for heart failure: evidence for electrical remodeling?", J Interv Card Electrophysiol., 2004, 10(1):47-50.

Vanderheyden et al., "Myocardial gene expression in heart failure patients treated with cardiac resynchronization therapy responders versus nonresponders", J. Am. Coll. Cardiol., 2008, 51(2) 129-136.

Wang et al., "Effect of Cardiac Resynchronization Therapy on Myocardial Fibrosis and Relevant Cytokines in a Canine Model With Experimental Heart Failure", J. Cardiovasc. Electrophysiol., 2017, 28(4):438-445.

Celikyurt et al., "Association between resolution of fragmented QRS and response to cardiac resynchronization therapy", Ann Noninvasive Electrocardiol., 2015 Jul. 7, 2014; 20(2): 126-31.

Das et al., "Fragmented wide QRS on a 12-lead ECG: a sign of myocardial scar and poor prognosis", Circ Arrhythm Electrophysiol., 2008, 1(4):258-268.

Das et al., "Fragmented QRS: a predictor of mortality and sudden cardiac death", Heart Rhythm, 2009, 6(3 Suppl): S8-14.

Das et al., "Automated Quantification of Low-Amplitude Abnormal QRS Peaks From High-Resolution ECG Recordings Predicts Arrhythmic Events in Patients With Cardiomyopathy", Circ Arrhythm Electrophysiol., 2017, 10(7):e004874 (pp. 1-12).

Lang et al., "Recommendations for cardiac chamber quantification by echocardiography in adults: an update from the American Society of Echocardiography and the European Association of Cardiovascular Imaging", J Am Soc Echocardiogr., Jan. 2015; 28(1) :1-39.

Yancy et al., "2013 ACCF/AHA guideline for the management of heart failure: A report of the American College of Cardiology Foundation/American Heart Assoc Task Force on Practice Guidelines", J. Am. Coll. Cardiol. 2013, 62(16):e147-239.

Suszko et al., "Quantifying abnormal QRS peaks using a novel time-domain peak detection algorithm: Application in patients with cardiomyopathy at risk of sudden death", 2015 IEEE International Conference on Electro/Information Technology (EIT), May 21-23, 2015; pp. 20-24.

International Search Report and Written Opinion dated Jul. 6, 2016 in International Patent Application No. PCT/CA2016/050567 (10 pages).

Endt et al., "Fragmentation of bandpass-filtered QRS-complex of patients prone to malignant arrhythmia", Medical and Biological Engineering and Computing, Nov. 1998, 36(6): 723-728.

Reikkenen et al., "Body position, electrode level, and respiration effects on the Frank lead electrocardiogram", Circulation, 1976, 53(1): 40-45.

Lander et al., "Analysis of abnormal intra-QRS potentials improved predictive value for arrhythmic events with the signal-averaged electrocardiogram", Circulation, 1997, 95(6): 1386-1393.

Lin et al., "Enhancement of accuracy and reproducibility of parametric modeling for estimating abnormal intra-QRS potentials in signal-averaged electrocardiograms," Medical engineering & physics, 2008, 30(7): 834-842.

Korhonen et al., "Fragmented QRS in prediction of cardiac deaths and heart failure hospitalizations after myocardial infarction," Annals of Noninvasive Electrocardiology, 2010, 15(2): 130-137.

Pan et al., "A real-time QRS detection algorithm," IEEE Transactions on Biomedical Engineering, 1985, BME-32(3): 230-236.

Dobbs et al., "QRS detection by template matching using real-time correlation on a microcomputer," Journal of clinical engineering, 1984, 9(3): 197-212.

Meyer et al., "Electrocardiogram baseline noise estimation and removal using cubic splines and state-space computation techniques," Computers and Biomedical Research, 1977, 10(5): 459-470.

Breithardt et al., "Standards for analysis of ventricular late potentials using high-resolution or signal-averaged electrocardiography: a statement by a task force committee of the European Society of Cardiology, the American Heart Association, and the American College of Cardiology," Journal of the American College of Cardiology, 1991, 17(5): 999-1006.

Gomis et al., "Analysis of abnormal signals within the QRS complex of the high-resolution electrocardiogram", IEEE Transactions on Biomedical Engineering, Aug. 1997, 44(8): 681-693.

Breslow, "Analysis of Survival Data under the Proportional Hazards Model", International Statistical Review / Revue Internationale de Statistique, 1975, 43(1): 45-57.

Lee et al., "Investigators of the Ontario ICD Database. Clinical Risk Stratification for Primary Prevention Implantable Cardioverter Defibrillators", Circ. Heart Fail., Sep. 2015, 8(5): 927-37.

Das et al., "Fragmented QRS on a 12-lead ECG: A predictor of mortality and cardiac events in patients with coronary artery disease", Heart Rhythm, 2007, 4: 1385-1392.

Zheng et al., "Sudden Cardiac Death in the United States, 1989 to 1998", Circulation, 2001, 104: 2158-2163.

Extended European Search Report issued in EP Patent Application No. 19795788.9 dated Jan. 27, 2022 (8 pages).

\* cited by examiner

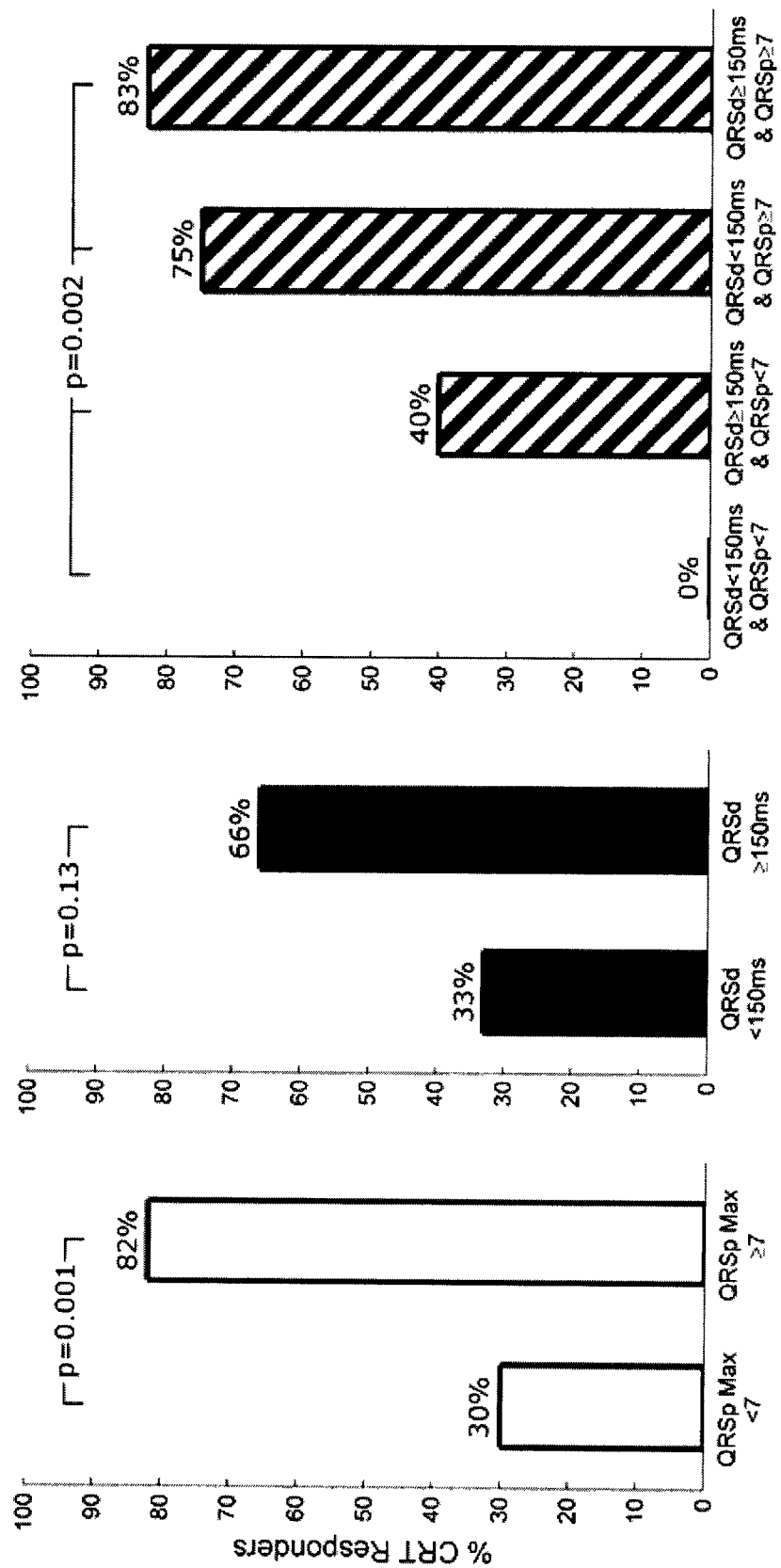

SYSTEM AND METHOD FOR ASSESSING QRS COMPONENTS AND LIKELIHOOD OF RESPONSE TO CARDIAC RESYNCHRONIZATION THERAPY

CROSS-REFERENCE TO RELATED APPLICATIONS

This application is a 35 USC § 371 national stage entry of International Patent Application No. PCT/CA2019/050563, filed Apr. 30, 2019, which claims priority from U.S. Provisional Patent Application Ser. No. 62/666,766, filed May 4, 2018, the entire contents of each of which are hereby incorporated by reference.

FIELD

Various embodiments are described herein that generally relate to a system and method for assessing QRS components, and in particular systems and methods for determining the likelihood of response to cardiac resynchronization therapy (CRT) and guiding the selection of CRT candidates amongst individuals with heart failure.

BACKGROUND

Heart failure is a chronic progressive cardiac condition affecting tens of millions of individuals globally and it is increasing in prevalence. CRT is a technique that has been shown to restore electromechanical ventricular synchrony, reverse structural remodeling and improve clinical outcomes in heart failure patients (see Russo et al. 2013). QRS duration >120 ms is traditionally used to select patients for CRT, among other clinical variables, however current CRT response rates are only 50-70%, which highlights the need to improve CRT patient selection. Although the presence of QRS fragmentation has been associated with ventricular dyssynchrony (see Sinha et al. 2016 and Tigen et al. 2009), its ability to predict patient response to CRT has been inconsistent (see Rickard et al. 2011 and Culikyurt et al. 2012). This lack of consistency may be attributed to the inability of the traditional qualitative analysis of QRS fragmentation from low resolution electrocardiograms (ECG) to discern small localized regions of dyssynchrony.

SUMMARY OF VARIOUS EMBODIMENTS

In a broad aspect, at least one embodiment described herein provides a method of assessing the likelihood of response to cardiac resynchronization therapy (CRT) for a patient. The method can include receiving ECG data obtained from the patient; analyzing the ECG data to detect abnormal QRS peaks; determining a likelihood of CRT response for the patient based on the detected abnormal QRS peaks; and providing an indication that the patient is a candidate for CRT based on the likelihood of CRT response.

In some embodiments, the method may include acquiring the ECG data from the patient using a plurality of ECG recording leads.

In some embodiments, the act of analyzing the ECG data from a given ECG recording lead may include: generating a local QRS (IQRS) signal from X beats of ECG data; generating a global QRS (gQRS) signal from Y beats of ECG data, where X and Y are integers and the X beats of ECG data are contained in the Y beats of ECG data; and comparing the IQRS signal with the gQRS signal to detect the abnormal QRS peaks in the IQRS signal.

In some embodiments, the IQRS signal can be generated by applying time averaging to unfiltered X beats of preprocessed ECG data, and the gQRS signal is generated by filtering the Y beats of preprocessed ECG data using a smoothing filter and then applying time averaging to the filtered Y beats of ECG data, where the X beats of ECG data is a short data window and the Y beats of ECG data is a larger data window that is at least one order of magnitude larger than the short data window.

In some embodiments, the comparing may include: identifying positive and negative peaks in the IQRS and gQRS signals; determining abnormal positive peaks in the IQRS signal by counting the number of positive peaks in the IQRS signal while excluding the nearest or greatest amplitude IQRS peak within ±M msec of each positive peak in the gQRS signal; determining abnormal negative peaks in the IQRS signal by counting the number of negative peaks in the IQRS signal while excluding the nearest or least amplitude IQRS peak within ±M msec of each negative peak in the gQRS signal; and determining a QRS peak (QRSp) score as the total of the abnormal positive peaks and the abnormal negative peaks in the IQRS signal.

In some embodiments, the QRSp score for the patient may be a mean, median or maximum of the QRSp scores for ECG data obtained from at least a portion of the ECG recording leads.

In some embodiments, the ECG data may include several sets of ECG data obtained using different ECG leads and the QRSp score can be determined for each set of ECG data.

In some embodiments, the ECG data may include precordial ECG data obtained using precordial leads.

In some embodiments, the act of determining the likelihood of CRT response for the patient may include determining a likelihood measure for the patient using the QRSp score for the patient in a statistical classification model that is generated using QRSp scores from patients with heart failure who do not respond to CRT and patients with heart failure who respond to CRT.

In some embodiments, the statistical classification model may be generated using the QRSp scores and at least one other clinical variable from the patients with heart failure who do not respond to CRT and the patients with heart failure who respond to CRT, and determining the likelihood measure may include using the QRSp score and the at least one other clinical variable from the patient in the statistical classification model.

In some embodiments, the statistical classification model may include one of a multivariable regression model, a decision tree model, a neural network model and a support vector machine model.

In some embodiments, the act of determining the likelihood of CRT response for the patient may include comparing the QRSp score to a CRT peak threshold.

In some embodiments, the QRSp score may be the maximum of the QRSp scores for ECG data obtained from the at least a portion of the ECG recording leads and the CRT peak threshold is at least 7.

In some embodiments, the method may further include performing CRT on the patient in response to the indication of likelihood of CRT response.

In some embodiments, the method may further include: receiving subsequent ECG data obtained from the patient following the performance of CRT on the patient; analyzing the subsequent ECG data to detect subsequent abnormal QRS peaks; comparing the number of subsequent abnormal QRS peaks to the number of abnormal QRS peaks; and providing an indication of a change in the number of abnormal QRS peaks based on the comparison.

In some embodiments, the method may further include modifying the patient's treatment regimen in response to the change in the number of abnormal QRS peaks.

In a broad aspect, at least one embodiment described herein provides a system identifying the likelihood of CRT response to guide CRT candidate selection. The system can include an input interface for receiving ECG data obtained from a patient; an output interface for providing a measure of likelihood of CRT response for the patient; and a processing unit coupled to the input and the output interfaces, the processing unit being configured to analyze the ECG data to detect abnormal QRS peaks; determine a likelihood of CRT response for the patient based on the detected abnormal QRS peaks; and to provide an indication that the patient is a candidate for CRT based on the likelihood of CRT response.

In some embodiments, the system may include: a sensor unit comprising sensors for sensing ECG data from the patient during use; and a data acquisition unit coupled to the sensor unit and the processing unit for acquiring the sensed ECG data.

In some embodiments, the processing unit can be configured to perform the methods described herein.

In a broad aspect, at least one embodiment described herein provides a computer readable medium comprising a plurality of instructions that are executable on a processing unit of a device for adapting the device to implement a method assessing the likelihood of CRT response to guide CRT candidate selection, wherein the method is described herein.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

FIG. 5C shows a plot of the probability of CRT responsiveness in patients having a number of abnormal QRS peaks below and at or above an example CRT peak threshold.

FIG. 5D shows a plot of the probability of CRT responsiveness in patients having a QRS duration below and at or above an example CRT duration threshold.

FIG. 5E shows a plot of the probability of CRT responsiveness in patients having various combinations of numbers of abnormal QRS peaks and QRS durations.

Figure 1:
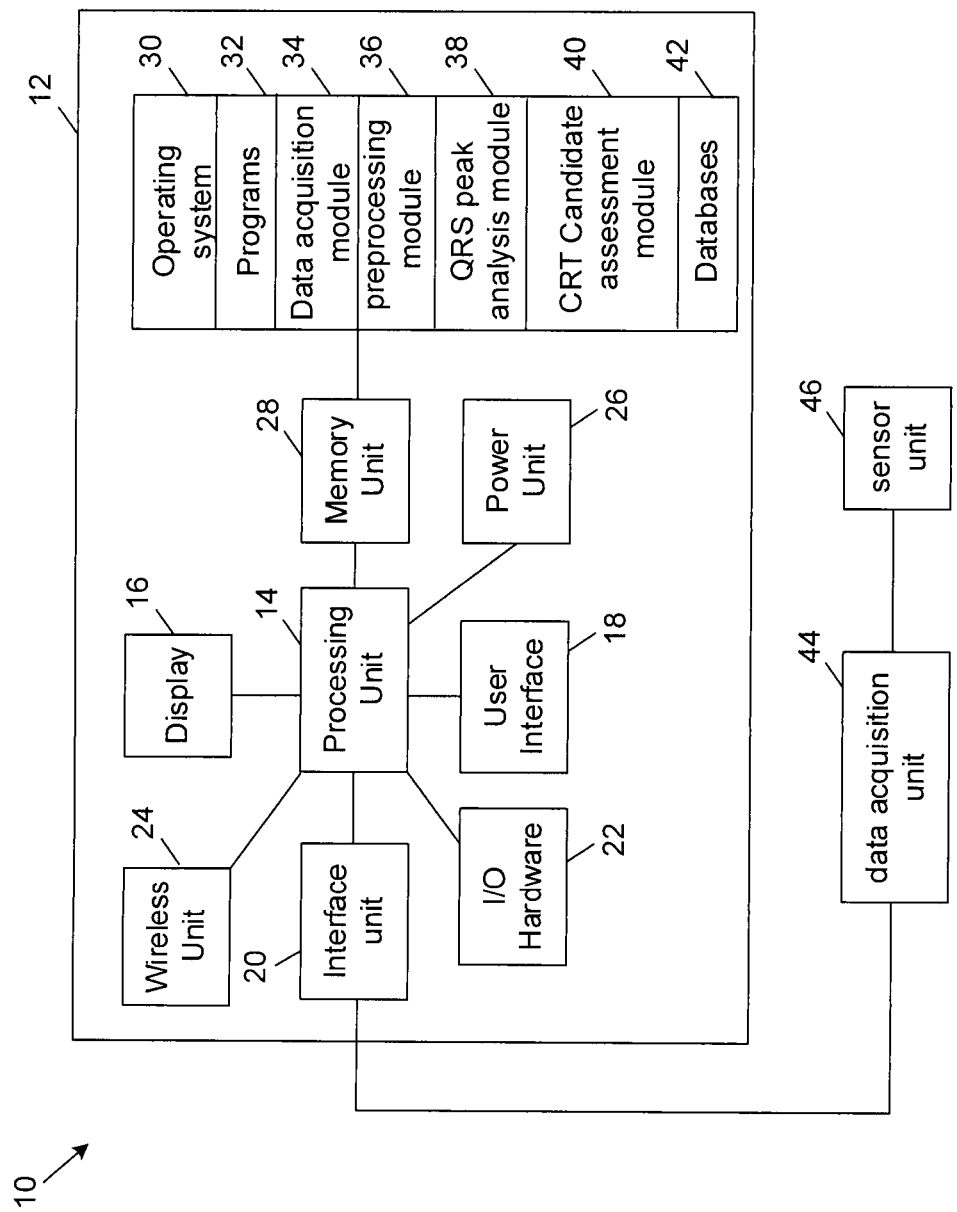
FIG. 1 is a block diagram of an example embodiment of a system for analyzing cardiac signals to assess the likelihood of CRT response.

Further aspects and features of the example embodiments described herein will appear from the following description taken together with the accompanying drawings.

DETAILED DESCRIPTION OF THE EMBODIMENTS

Various systems, devices or methods will be described below to provide an example of at least one embodiment of the claimed subject matter. No embodiment described herein limits any claimed subject matter and any claimed subject matter may cover systems, devices or methods that differ from those described herein. The claimed subject matter is not limited to systems, devices or methods having all of the features of any one process or device described below or to features common to multiple or all of the systems, devices or methods described herein. It is possible that a system, device or method described herein is not an embodiment of any claimed subject matter. Any subject matter that is disclosed in a system, device or method described herein that is not claimed in this document may be the subject matter of another protective instrument, for example, a continuing patent application, and the applicants, inventors or owners do not intend to abandon, disclaim or dedicate to the public any such subject matter by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending on the context in which these terms are used. For example, the terms coupled or coupling can have a mechanical, electrical or communicative connotation. For example, as used herein, the terms coupled or coupling can indicate that two or more elements or devices can be directly connected to one another or connected to one another through one or more intermediate elements or devices via an electrical element, electrical signal or a mechanical element depending on the particular context. Furthermore, the term "communicative coupling" indicates that an element or device can electrically, optically, or wirelessly send data to or receive data from another element or device.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term such as 1%, 2%, 5% or 10%, for example, if this deviation does not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed, such as 1%, 2%, 5% or 10%, for example.

The example embodiments of the systems, devices or methods described in accordance with the teachings herein may be implemented as a combination of hardware or software. For example, the embodiments described herein may be implemented, at least in part, by using one or more computer programs, executing on one or more programmable devices comprising at least one processing element, and at least one data storage element (including volatile and non-volatile memory and/or storage elements). These devices may also have at least one input device (e.g. a keyboard, a mouse, a touchscreen, and the like), and at least one output device (e.g. a display screen, a printer, a wireless radio, and the like) depending on the nature of the device.

It should also be noted that there may be some elements that are used to implement at least part of the embodiments described herein that may be implemented via software that is written in a high-level procedural language such as object oriented programming. The program code may be written in C, C++ or any other suitable programming language and may comprise modules or classes, as is known to those skilled in object oriented programming. Alternatively, or in addition thereto, some of these elements implemented via software may be written in assembly language, machine language or firmware as needed. In either case, the language may be a compiled or interpreted language.

At least some of these software programs may be stored on a storage media (e.g. a computer readable medium such as, but not limited to, ROM, magnetic disk, optical disc) or a computing device that is readable by a general or special purpose programmable device having a processor, an operating system and the associated hardware and software that is necessary to implement the functionality of at least one of the embodiments described herein. The software program code, when read by the computing device, configures the computing device to operate in a new, specific and predefined manner in order to perform at least one of the methods described herein.

Furthermore, at least some of the programs associated with the systems and methods of the embodiments described herein may be capable of being distributed in a computer program product comprising a computer readable medium that bears computer usable instructions, such as program code, for one or more processors. The medium may be provided in various forms, including non-transitory forms such as, but not limited to, one or more diskettes, compact disks, tapes, chips, and magnetic and electronic storage. In alternative embodiments, the medium may be transitory in nature such as, but not limited to, wire-line transmissions, satellite transmissions, Internet transmissions (e.g. downloads), media, digital and analog signals, and the like. The computer useable instructions may also be in various formats, including compiled and non-compiled code.

Heart failure is a chronic progressive cardiac condition affecting millions of North Americans and increasing in prevalence. Various therapeutic options (e.g. medical treatment regimens and surgical intervention options) exist to treat various forms of heart disease and heart failure. However, the selection of specific medications and/or surgical interventions for individual patients can play a large role in the outcomes experienced by those patients. For instance, doctors may often decide between alternative medication regiments or instituting different cardiac interventions such as cardiac surgery, percutaneous coronary intervention, catheter ablation and/or defibrillator therapy.

Different patients may be more or less responsive to different types of treatments, however, in many cases it is difficult to determine ahead of treatment whether an individual patient will respond to a specific course of treatment. Accordingly, patients may undergo surgical interventions that ultimately turn out to be ineffective or suboptimal. This puts a strain on medical resources, exposes the patient to unnecessary procedural risk, and prevents the patient from undertaking an alternative treatment regimen that is more likely to be effective in treating their condition.

Cardiac resynchronization therapy (CRT) is an example of a surgical intervention that has been shown to improve clinical outcomes in heart failure patients with New York Heart Association (NYHA) class II-III function, LV ejection fraction (LVEF)<35%, and QRS duration (QRSd)>120 ms (see Russo et al. 2013). However, there is still a large percentage (approximately 30-40%) of patients with these clinical criteria who do not respond to CRT treatment (see Leyva et al., 2014). As a result, treating these patients using CRT may actually result in worse clinical outcomes as the opportunity to pursue alternative therapeutic options is delayed.

CRT restores electromechanical left ventricular (LV) synchrony and has been shown to reverse structural remodeling. Many patients may not respond to CRT as a result of minimal electromechanical dyssynchrony or suboptimal LV lead pacing/placement. In view of this, targeted LV lead implantation to sites of latest electrical or mechanical activation has improved CRT response rate (see Khan et al., 2012; Gold et al., 2011). However, the assessment of electromechanical dyssynchrony can be highly variable between clinicians, rendering it difficult to accurately identify patients for CRT and may account for the lack of consistent improvement in CRT response when using these metrics for patient selection. For instance, assessment of mechanical activation time and dyssynchrony based on echocardiographic-derived measures of regional strain and wall motion can be limited by large observer variability.

A number of techniques for evaluating activation time and dyssynchrony have been developed. However, these techniques may not provide a reliable prediction of whether a patient will respond to CRT.

In cases, electrical dyssynchrony has been evaluated using QRSd and bundle branch block (BBB) morphology. In general, the CRT response rate increases in patients with more prolonged QRSd and left BBB (LBBB) (see Birnie et al.; Hawkins et al., 2006). Nonetheless, LV activation timing can still be quite heterogeneous for any given QRSd or BBB morphology due to varying spatial/transmural scar mass, scar border zones of slow conduction and lines of functional conduction block (see Auricchio et al., 2004; Auricchio et al., 2014). Structural remodeling in this manner can change the direction of activating wavefronts in addition to delaying LV activation time, which can manifest on the surface 12-lead ECG as QRS fragmentation (see Flowers et al., 1969; Igarashi et al., 2017).

The presence of QRS fragmentation has been shown to predict mortality and sudden cardiac death in patients with coronary artery disease and cardiomyopathy (see Das et al., 2010). QRS fragmentation is also associated with echocardiographic-derived ventricular dyssynchrony (see Sinha et al., 2016; and Tigen et al., 2009), however its ability to predict CRT response has been inconsistent (see Rickard et al., 2011; Celikyurt et al., 2012). A potential limitation is the qualitative (i.e. present or absent) evaluation of QRS fragmentation (fQRS) based on manually-defined large intra-QRS deflection from a low resolution standard 12-lead ECG, which may not discern more localized, yet dyssynchronous myopathic regions. Methods to quantify smaller abnormal QRS components from high resolution ECGs have the potential to identify localized regions of dyssynchrony and therefore better discriminate patients who will respond to CRT.

As described herein, the inventors have developed techniques for assessing the likelihood of CRT response in heart failure patients by automatically identifying and quantifying abnormal QRS peaks (QRSp) in ECG data. The inventors have found that methods of automatically quantifying abnormal QRS peaks (QRSp) in high-resolution ECGs can be an independent predictor of CRT response in patients with cardiomyopathy. The techniques described herein can be implemented to improve selection of patients for CRT therapy.

Techniques for automatically detecting abnormal QRSp peaks are explained at length in Applicant's PCT Publication No. WO2016/183683 the entirety of which is hereby incorporated by reference. As described therein, QRS deflections which deviate from a smoothed QRS waveform can be identified as abnormal QRS peaks (referred to as QRSp). The inventors have found that quantification of these abnormal QRS peaks can provide an independent evaluation of a patient's functional response to CRT that is more predictive than existing ECG or clinical metrics. For example, quantification of the QRSp max for a patient has been found to be predictive of a patient's functional response to CRT.

Embodiments described herein generally relate to systems and methods for assessing the likelihood of response to cardiac resynchronization therapy (CRT) amongst heart failure patients to identify CRT candidates. The systems and methods described herein can use the results of time-domain based methods for quantifying abnormal QRS peaks using a short averaging window as a predictor for whether a patient is responsive to CRT. The number of abnormal QRS peaks identified using these methods can be used in conjunction with other clinical variables to calculate a likelihood of CRT response. The likelihood of CRT response can, in turn, be used to identify candidates likely to respond to CRT.

As described herein, a study was conducted to compare the predictive capability of time-domain based methods for quantifying abnormal QRS peaks with other ECG metrics that have been used to evaluate CRT responses in patients, such as QRSd, BBB morphology or fQRS.

The prospective study involved forty-seven patients (LVEF 23±7%) who underwent CRT. Digital high resolution (1024 Hz) 12-lead ECGs were recorded during native rhythm at baseline and 6 months post-CRT. For each precordial lead, QRSp was defined as the total number of peaks detected in the QRS minus those found on a smoothed moving average filtered version of the QRS using the methods described herein below. QRSp Max and QRSp Mean were calculated for each patient as the maximum and mean of their six precordial lead QRSp values, respectively. CRT response was defined as a >5% increase in LVEF post-CRT and occurred in 60% of patients.

Baseline QRSd was similar in responders and non-responders, and did not change post-CRT regardless of response. Baseline QRSp Max was greater in responders than non-responders (9.1±3.5 vs. 5.9±2.2, p=0.001) and decreased in responders (9.2±3.6 vs. 7.9±2.8, p=0.03) but increased in non-responders (5.5±2.3 vs. 7.5±2.8, p=0.049) post-CRT. In multivariable analysis, QRSp Max was the only independent predictor of CRT response (Odds Ratio [95% Confidence Interval]:1.5[1.1-2.1], p=0.01). ROC analysis revealed that QRSp Max (AUC=0.80) and QRSd (AUC=0.67) can accurately discriminate response. Compared to QRSd≥150 ms, QRSp Max≥7 identified response with similar sensitivity but greater specificity (74% vs. 32%, p<0.05). Amongst patients with QRSd<150 ms, more patients with QRSp Max≥7 responded than those with QRSp Max<7 (75% vs. 0%, p<0.05).

The results of the study further show that the disclosed methods for automatically quantifying abnormal QRS peaks (QRSp) from high-resolution ECGs are an independent predictor of CRT response in patients with heart failure. Furthermore, the study results indicate that a CRT threshold of QRSp Max≥7 can identify CRT responders with similar sensitivity as QRSd, but with significantly greater specificity. Additionally, for each additional QRSp Max detected, the study shows that the odds of a patient responding to CRT increased by 1.6 fold.

In some embodiments described herein, QRSp may also be used to monitor recovery in patients undergoing CRT. The inventors have found that long-term changes in QRSp track mechanical recovery in CRT responders. Accordingly, in some embodiments described herein, changes in a patient's QRSp following CRT can be used to evaluate a patient's response to CRT. For example, the degree of change in QRSp following CRT may be used to guide and/or modify therapeutic decisions in heart failure patients such as modifying medications, optimizing CRT pacing parameters, revising the position of the CRT pacing leads, or discontinuing CRT pacing altogether.

Referring now to FIG. 1, shown therein is a block diagram of an example embodiment of a patient evaluation system 10 that may be used to analyze cardiac signals to assess a patient's likelihood of responding to CRT and evaluate whether the patient is a candidate for CRT. The patient evaluation system 10 may also be used to monitor patient responses to CRT to evaluate the effectiveness of the CRT treatment.

The patient evaluation system 10 includes an operator unit 12 that has at least one input for receiving cardiac electrical data; at least one processing unit for processing the cardiac electrical data to determine the electrical substrate, evaluate whether a patient is a candidate for CRT, and evaluate a patient's response to CRT; and at least one output for providing an indication of electrical substrate and whether the patient is a candidate for CRT.

The patient evaluation system 10 is provided as an example and there may be other embodiments of the system 10 with different components or a different configuration of the components described herein. The system 10 further includes several power supplies (not all shown) connected to various components of the treatment planning system 10 for providing power thereto as is commonly known to those skilled in the art.

In general, a user may interact with the operator unit 12 to analyze cardiac electrical data from a patient to determine whether the patient is likely to respond to CRT, and thus whether the patient is a candidate for CRT. After the analysis, the user can then use the operator unit 12 to provide, display and/or store an indication of whether the patient is a candidate for CRT. For patients having already undergone CRT, the user may also use the operator unit 12 to evaluate the patient's response to CRT. In some cases, the user may use the system 10 to obtain cardiac electrical data from the patient using appropriate sensors and data acquisition hardware and software.

Figure 2:
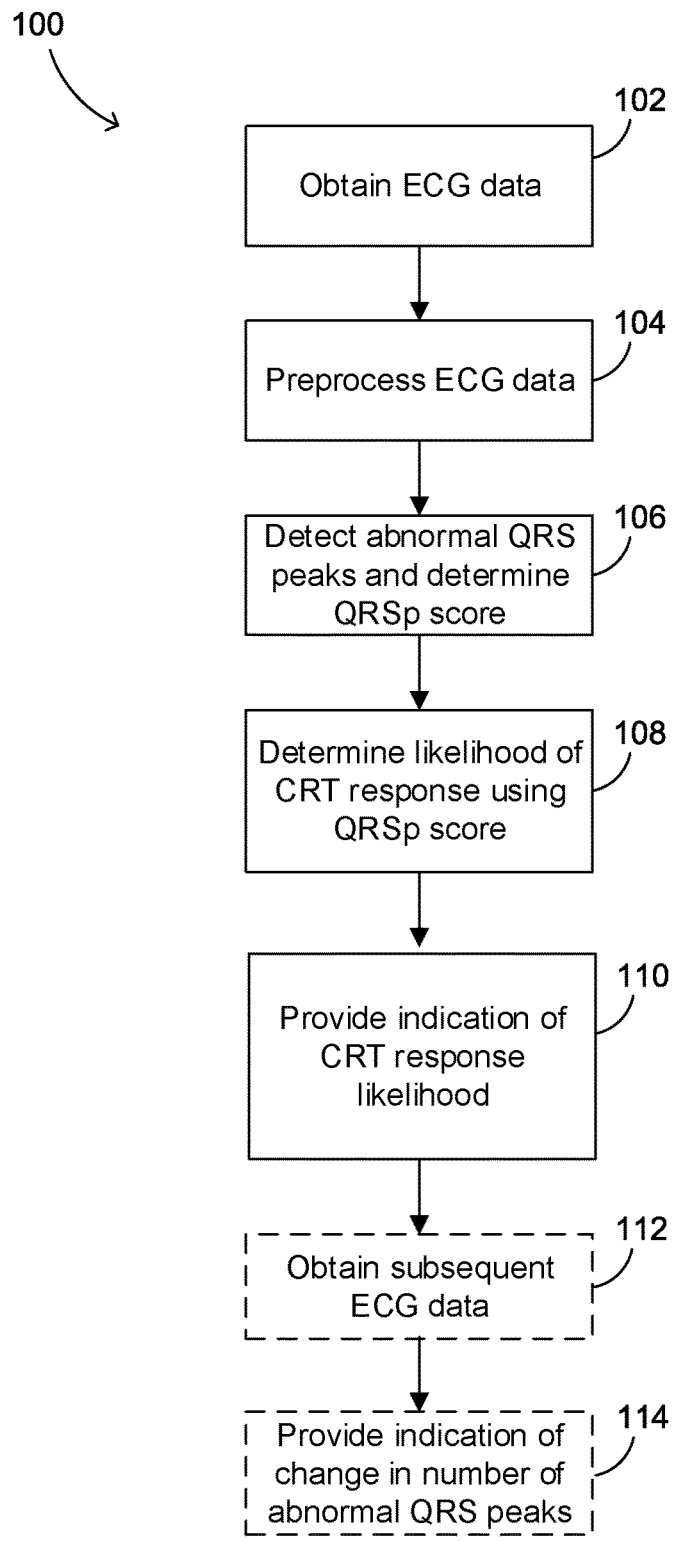
FIG. 2 is a flowchart of an example embodiment of a method for analyzing cardiac signals to assess the likelihood of CRT response.

The operator unit 12 comprises a processing unit 14, a display 16, a user interface 18, an interface unit 20, Input/Output (I/O) hardware 22, a wireless unit 24, a power unit 26, and a memory unit 28. The memory unit 28 comprises software code for implementing an operating system 30, various programs 32, a data acquisition module 34, a pre-processing module 36, a QRS peak analysis module 38, a CRT candidate assessment module 40, and one or more databases 42. Modules 34 to 40 will be described in greater detail with respect to FIG. 2. Some of the modules may be combined in some embodiments. Many components of the operator unit 12 can be implemented using a desktop computer, a laptop, a mobile device, a tablet, and the like.

In some embodiments, in which ECG data is to be obtained from a patient, the system 10 further comprises a data acquisition unit 44 and a sensor unit 46, which are described in further detail below.

The processing unit 14 controls the operation of the operator unit 12 and can be a suitable processor, controller or digital signal processor that can provide sufficient processing power depending on the configuration and operational requirements of the patient evaluation system 10. For example, the processing unit 14 may be a high performance processor. In alternative embodiments, the processing unit 14 may include more than one processor with each processor being configured to perform different dedicated tasks. In alternative embodiments, specialized hardware can be used to provide some of the functions provided by the processing unit 14.

The display 16 can be any suitable display that provides visual information depending on the configuration of the operator unit 12. For instance, the display 16 can be a cathode ray tube, a flat-screen monitor and the like if the operator unit 12 is a desktop computer. In other cases, the display 16 can be a display suitable for a laptop, tablet or a handheld device such as an LCD-based display and the like.

The user interface 18 can include at least one of a mouse, a keyboard, a touch screen, a thumbwheel, a track-pad, a track-ball, a card-reader, voice recognition software and the like again depending on the particular implementation of the operator unit 12. In some cases, some of these components can be integrated with one another.

The interface unit 20 can be any interface that allows the operator unit 12 to communicate with other devices or systems. In some embodiments, the interface unit 20 may include at least one of a serial bus or a parallel bus, and a corresponding port such as a parallel port, a serial port or a USB port that provides USB connectivity. The busses may be external or internal. The busses may be at least one of a SCSI, USB, IEEE 1394 interface (FireWire), Parallel ATA, Serial ATA, PCIe, or InfiniBand. Other communication protocols may be used by the bus in other embodiments. The host interface component 134 may use these busses to connect to the Internet, a Local Area Network (LAN), a Wide Area Network (WAN), a Metropolitan Area Network (MAN), a Wireless Local Area Network (WLAN), a Virtual Private Network (VPN), or a peer-to-peer network, either directly or through a modem, router, switch, hub or other routing or translation device.

The I/O hardware 22 is optional and can include, but is not limited to, at least one of a microphone, a speaker, a keyboard, a mouse, a touch pad, a display device and a printer, for example.

The wireless unit 24 is optional and can be a radio that communicates utilizing CDMA, GSM, GPRS or Bluetooth protocol according to standards such as IEEE 802.11a, 802.11b, 802.11g, or 802.11n. The wireless unit 24 can be used by the operator unit 12 to communicate with other devices or computers.

The power unit 26 can be any suitable power source that provides power to the operator unit 12 such as a power adaptor or a rechargeable battery pack depending on the implementation of the operator unit 12 as is known by those skilled in the art.

The memory unit 28 can include RAM, ROM, one or more hard drives, one or more flash drives or some other suitable data storage elements such as disk drives, etc. The memory unit 28 may be used to store the operating system 30 and programs 32 as is commonly known by those skilled in the art. For instance, the operating system 30 provides various basic operational processes for the operator unit 12. The programs 32 include various user programs so that a user can interact with the operator unit 12 to perform various functions such as, but not limited to, acquiring data, pre-processing data, analyzing preprocessed data, assess a likelihood of response to CRT, determining whether a patient is a candidate for CRT based on the analysis and/or evaluating a patient's response to CRT based on the analysis as well as viewing, manipulating, communicating and storing data as the case may be.

The data acquisition module 34 may be used to obtain cardiac electrical data (e.g. bipolar and unipolar body surface ECG, bipolar and unipolar intracardiac electrograms) from a patient. The preprocessing module 36 then preprocesses the cardiac electrical data so that it may be analyzed more accurately. The QRS peak analysis module 38 then analyzes the preprocessed cardiac electrical data to determine the abnormal QRS peaks. The CRT candidate assessment module 40 then determines a patient's likelihood of responding to CRT, based on the abnormal QRS peaks, may determine whether the patient is a candidate for CRT and may evaluate the patient's response following CRT. The operation of the modules 34 to 40 will be discussed in more detail in relation to the description of FIG. 2. It should be noted that the various modules 34 to 40 may be combined or further divided into other modules. The modules 34 to 40 are typically implemented using software, but there may be some instances in which at least some of these modules are implemented using FPGA or application specific circuitry.

The databases 42 can be used to store data for the system 10 such as system settings, parameter values, and calibration data. The databases 42 can also store other information required for the operation of the programs 32 or the operating system 30 such as dynamically linked libraries and the like. The databases 42 may also be used to store data on patients from which electrogram data has been obtained and the results of QRS peak analysis.

The operator unit 12 comprises at least one interface that the processing unit 14 communicates with in order to receive or send information. This interface can be the user interface 18, the interface unit 20 or the wireless unit 24. For instance, the amount of cardiac electrical data, as well as the recording, processing and analysis parameters that may be used by the system 10 may be inputted by a user or otherwise selected through the user interface 18 or this information may be received through the interface unit 20 from a computing device. The processing unit 14 can communicate with either one of these interfaces as well as the display 16 or the I/O hardware 22 in order to use this input information to analyze cardiac electrical data obtained from a patient and in some cases to obtain and preprocess the cardiac electrical data from the patient. In addition, users of the operator unit 12 may communicate information across a network connection to a remote system for storage and/or further analysis of trials and their associated results in some embodiments.

A user can also use the operator unit 12 to provide information needed for system parameters that are needed for proper operation of the system 10 such as calibration information and other system operating parameters as is known by those skilled in the art. The user may also use the operator unit 12 to modify likelihood criteria for the system 10, such as variables used in a statistical likelihood model. Data that is obtained from patients, as well as parameters used for operation of the system 10, may be stored in the memory unit 28. The stored data may include raw sampled data as well as processed cardiac electrical data, and/or analyzed data.

The data acquisition unit 44 comprises hardware circuitry that is needed to record cardiac electrical data from a patient. Different variations are possible for the data acquisition unit 44 as is known by those skilled in the art. For example, the data acquisition unit 44 may comprise a multi-channel digital data acquisition system with a controller and one or more data acquisition boards each having a certain number of recording channels. Each data acquisition board may generally comprise an amplifier bank, a filter bank, a multiplexer, an Analog to Digital Controller (ADC) and a DSP unit. The DSP unit may be implemented by one or more processors or by specialized circuitry as is known by those skilled in the art.

In use, data measured by a given recording channel is amplified by a corresponding amplifier in the amplifier bank, filtered by a corresponding filter in the filter bank, multiplexed by the multiplexer, and then digitized by the ADC. The individual gains of the amplifiers in the amplifier bank may be applied to groups of channels and may be automatically set by the processing unit 14 or an on-board DSP unit in the data acquisition unit 44 that receives commands from the operator unit 12 via a communication link (such as, but not limited to an RS-232 link, for example). Data and commands may be exchanged between the one or more acquisition boards and the processing unit 14 via one or more buses.

During data acquisition, the data acquisition unit 44 obtains cardiac electrical data and sends the cardiac electrical data through a link to the operator unit 12 for storage and analysis. A multiplexer circuit may be used to interface all of the data acquisition boards. The processor or on-board DSP unit may also control the data acquisition parameters (e.g. amplifier gains, filter coefficients, detection threshold and sampling sequence during data acquisition). Sampling rates may be set to at least 1,000 Hz and analog filters may be set to have a passband of about 0.05-400 Hz. In addition, amplifiers may be selected so that the common mode rejection ratio on the bipolar and unipolar channels is greater than about 90 dB from DC to 1,000 Hz, which is sufficient for 12 bit resolution. In some cases, the front end of the data acquisition unit 44 may be battery-operated, providing full electrical isolation.

The sensor unit 46 may be used to record cardiac signals, such as body surface ECG signals or intracardiac signals, from which ECG data is derived. The electrodes can be standard ECG electrodes, carbon electrodes, platinum electrodes, silver-silver chloride electrodes, or variations thereof. The electrodes can be configured in the standard 12-lead configuration or Frank lead vectorial configuration. Alternatively, the number of ECG electrodes and their body surface configuration can be varied, such as in multielectrode thorax body surface mapping. These electrode sensors can be configured to record body surface or intracardiac electrical potentials in either a bipolar or unipolar configuration.

Referring now to FIG. 2A, shown therein is a flowchart of an example embodiment of a method 100 for analyzing cardiac signals to determine whether a patient is likely to be responsive to cardiac resynchronization therapy (CRT). Method 100 may be used to identify patients who are likely to respond to CRT as candidates for CRT. This may generally include obtaining and preprocessing ECG data, determining whether a patient is likely to respond to CRT by analyzing the preprocessed ECG data to determine abnormal QRS peaks, and then providing an indication of the abnormal QRS peaks and/or the likelihood of response to CRT. Based on the likelihood of response to CRT, an indication of whether or not the patient is a candidate for CRT may be provided. Therapeutic decisions can be made based on the likelihood of response to CRT, or the indication that the patient is a candidate for CRT, such as performing CRT or alternative treatment measures such altering a patient's medications or instituting different surgical interventions.

This analysis may be done for different portions of ECG readings obtained from different areas of the patient's body surface or heart. For example, QRS peak detection may be done in consecutive 10 to 50 beat windows and the number of abnormal QRS peaks (QRSp) in each ECG recording over a 100 to 500 beat recording sequence may be determined.

The patient treatment evaluation method 100 starts with obtaining ECG data at act 102 in which the sensor unit 46 is applied to a patient or subject to measure ECG data using a plurality of leads placed on the body surface or within the heart. The data acquisition module 34 in combination with the data acquisition unit 44 and the sensor unit 46 may be used at 102. Unipolar lead configuration (e.g. precordial leads V1-V6) may be preferable since each lead provides an independent recording. However, in alternative embodiments, a bipolar lead configuration may be used. The ECG data is obtained using a sufficient sampling rate and resolution to identify abnormal QRS peaks according to the teachings herein. For example, high resolution ECG data is preferable, which may be obtained using a sampling rate of at least 1,000 Hz.

At act 104, the ECG data is preprocessed. The preprocessing may include using a QRS template matching stage followed by an ECG signal filtering stage. This processing may be done by the preprocessing module 36.

For example, in at least some embodiments, a QRS template may be constructed for each ECG recording lead by manually or automatically defining the QRS start and end points on a representative QRS complex (e.g. a QRS complex resulting from native or intrinsic electrical conduction of the heart as opposed to a QRS complex derived from a premature beat or fusion beat or artifact). In other embodiments, an automatic QRS start and end detector may be implemented. The earliest QRS onset found in any lead may be used as the template start point for each lead and the latest QRS offset found in any lead may be used as the template end point for each lead. The QRS template may be aligned and compared with each QRS complex to identify morphologically dissimilar beats (i.e. QRS beats arising from premature beats, fusion beats or artifacts) that are excluded from analysis. The R wave location of each QRS complex in the ECG may be identified using the Pan and Tompkins automated peak detection method, in at least some embodiments. However, other methods to identify R wave location may also be used in some embodiments, such as, but not limited to, one of wavelet transformation, neural networking, or dictionary-based comparative methods. For each beat in the ECG recording, which may be 3 minutes long for example, the R wave of the template may be aligned with the R wave of the individual beat.

The alignment can be achieved using cross-correlation of a moving window that may be incremented by a single sample point from a certain time before to a certain time after the initial alignment position, such as 25 msec before to 25 msec after, for example. The temporal point that produces the greatest average correlation coefficient (between the QRS complexes and template) for all ECG leads can be set as the optimal alignment position (QRS templating and alignment can be done separately for each lead). Once QRS complexes are aligned, those QRS complexes that do not achieve a pre-specified cross-correlation with the template, such as >90%, on all ECG leads, are excluded from analysis because they do not sufficiently match the morphology of the template. This process may be repeated until a certain number of QRS complexes matching the template have been identified, such as 100 to 500 QRS complexes, for example. These template-matched QRS complexes are saved for further processing.

In at least some embodiments, QRS complexes with a ST segment root mean square noise value above a certain threshold can be excluded. This threshold may be 10 μV, for example, although others may be used. This may minimize false QRS peak detection.

In at least some embodiments, the entire ECG recording may be filtered after template matching to further eliminate noise. For example, to attenuate high frequency noise, a lowpass filter may be applied to the ECG data after template matching. The lowpass filter may be a 4th order (Butterworth) bidirectional lowpass filter with a 150 Hz cutoff frequency, for example, although others may be used.

In at least some embodiments, the ECG filtering may further include removing low frequency baseline wander by applying cubic spline correction. Spline anchors may be placed in the isoelectric PR segment at a certain point prior to the aligned onset of each QRS complex, such as 15-25 ms, for example and preferably 20 ms. A cubic spline may then be fit to the anchor points and subtracted from the original ECG recordings to remove the baseline wander.

It should be noted that acts 102 and 104 may be optional in that the method 100 may be applied to ECG data that has already been obtained and preprocessed. In this case, the preprocessed ECG data is loaded from a data source, such as a data store, and the method starts at act 106.

At act 106, the method 100 comprises analyzing the preprocessed ECG data to detect abnormal QRS peaks, referred to hereafter as abnormal QRSp, that actually perturb the underlying QRS morphology. At act 106, the method 100 can also determine scores for abnormal QRSp.

This detection may be done for ECG data recorded from one ECG lead or multiple ECG leads. For example, scores for abnormal QRSp, hereafter referred to generally as QRSp scores may be determined. There are several different types of QRSp scores that may be determined as described below. For example, scores for abnormal QRSp may be separately determined for smaller time windows of ECG data for each lead, such as a 10 beat window, for example, where the smaller time window is slid along a larger time window having a larger number of beats, such as 100 beats, for example; in this case the abnormal QRSp score is a QRSp window (QRSpW) score. Each lead may then be assigned a QRSp lead (QRSpL) score which may be the mean, median or maximum of the QRSpW scores determined for each of the smaller windows of ECG data for that lead. The final QRSp score (QRSpF) that may be used for the patient or subject may be the QRSpL score from a single ECG lead, or may be based on a combination of the QRSpL scores from all or a subset of the ECG leads. The combination may be the mean, median or maximum QRSpL score across the ECG leads that are used for the QRSpF score. ECG data from a given lead may be chosen to determine the QRSpF score if the amount of noise in the ECG data for the given ECG lead is acceptable.

The detection of abnormal QRS peaks may be performed by the QRS peak analysis module 38. According to the teachings herein, abnormal QRSp may be distinguished from normal QRS peaks by comparing two preprocessed versions of the QRS complex, namely the local QRS average (lQRS) and the global QRS average (gQRS). The gQRS may be a smoothed QRS waveform generated by applying a smoothing filter, such as a 15-point bidirectional moving average filter, for example, to the ECG data from a lead and then performing averaging on a plurality of filtered QRS complexes such as from Y beats of ECG data. Other smoothing filters may be used in alternative embodiments such as, but not limited to, median filters, low pass FIR filters (e.g. Butterworth, Chebyshev, etc.) or wavelet based filters.

Typically, 100 to 500 filtered QRS complexes may be averaged, with 100 being preferable, for example. This produces the gQRS which is a smoothed QRS complex with low frequency contours, which constitute the normal QRS peaks. The IQRS may be generated by averaging a smaller number of unfiltered consecutive QRS complexes such as from X beats of ECG data. Typically 10 to 50 unfiltered QRS complexes may be averaged, with 10 being preferable, to obtain the IQRS. Unfiltered in this context means that there is no additional filtering after the preprocessing of the ECG data. The parameters X and Y are integers and the X beats of ECG data are contained in the Y beats of ECG data. Since the IQRS is unfiltered, it will contain both normal QRS peaks and abnormal QRS peaks.

Figure 3A:
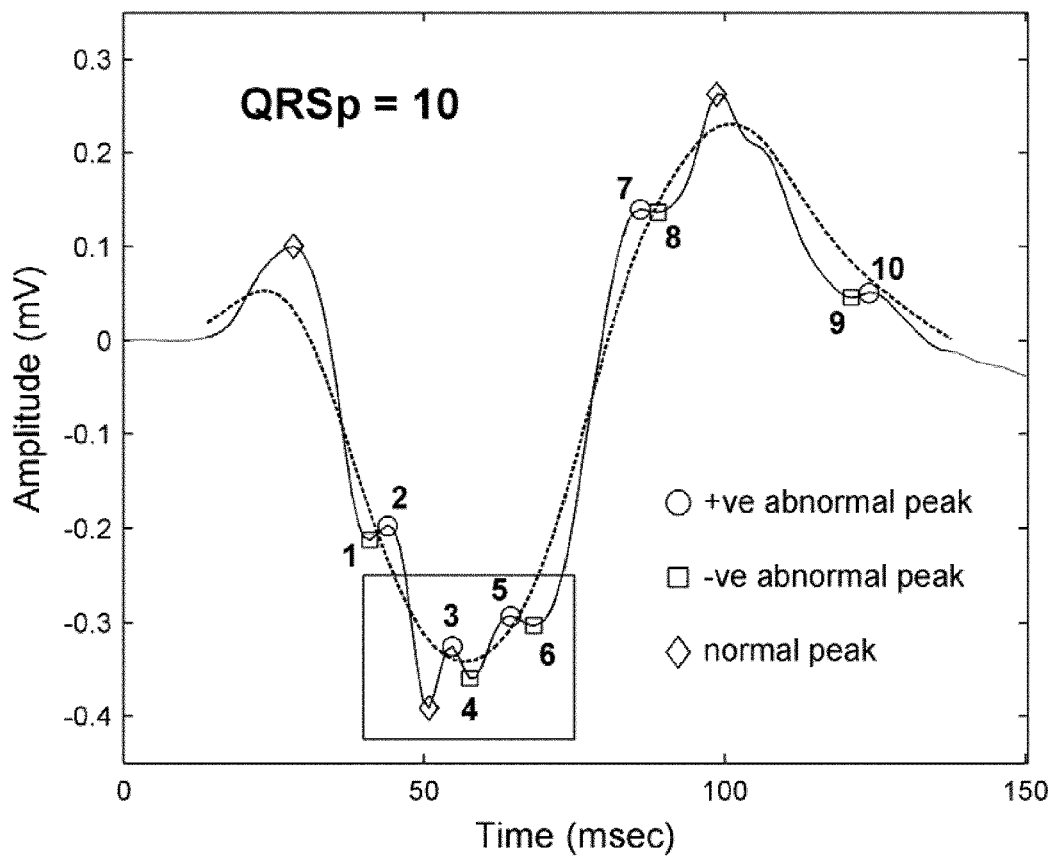
FIGS. 3A and 3B show detection of normal and abnormal QRS peaks from a precordial electrocardiogram recording of a heart failure patient with ischemic cardiomyopathy (ICM).
Figure 3B:
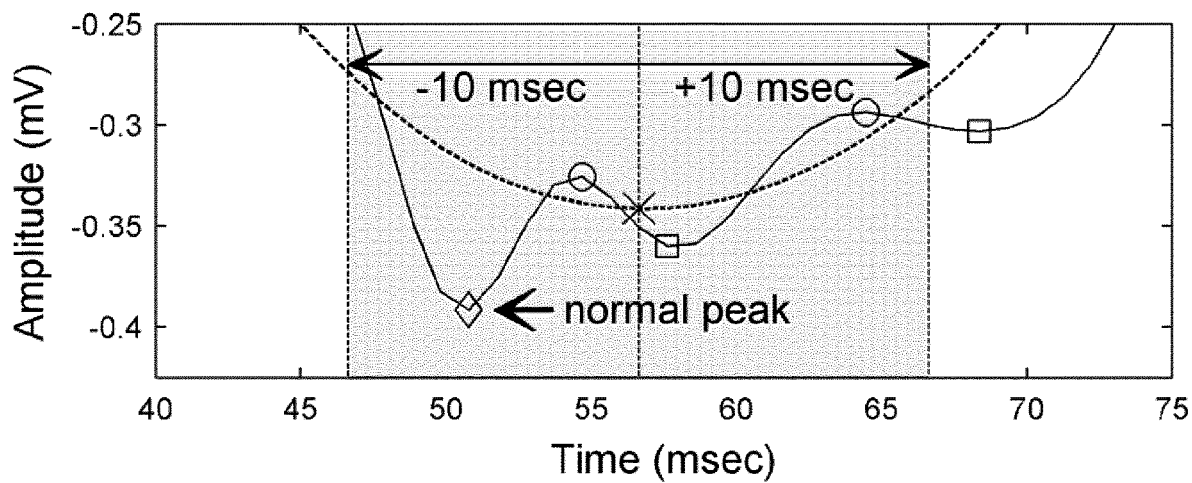

As illustrated in FIGS. 3A and 3B, abnormal QRSp may be defined by comparing the IQRS signal with the gQRS signal to detect the abnormal QRS peaks in the IQRS signal which may be all of the peaks in the IQRS complex that are not in the gQRS complex. This may be repeated by sliding a window of X beats of ECG data within the larger window of Y beats of ECG data.

In some embodiments, the X and Y beats of ECG data may be continuous in time. Alternatively, in some embodiments, the X and Y beats of ECG data may not be continuous as at least one intermediate beat of ECG data may be discarded for having too much noise.

The process of detecting abnormal QRS peaks is explained in detail in Applicant's PCT Publication No. WO2016/183683. In general, abnormal QRS peaks may be detected and a QRSpL score may be quantified independently for each ECG recording lead.

An IQRS signal (i.e. a shorter local QRS average of the ECG data for a given recording ECG lead) and a gQRS signal (i.e. a longer global QRS average of the ECG data for the given ECG recording lead) can be determined for a recording lead as described above. The set of all positive and negative peaks for the IQRS and the gQRS can be determined. A positive peak may be defined as any point where the preceding and subsequent ECG data samples have a lower amplitude than a current ECG data sample. A negative peak may be defined as any point where the preceding and subsequent ECG data samples have a greater amplitude than a current ECG data sample.

For each positive gQRS peak, the subset of positive IQRS peaks within ±X msec (which may be considered to be a proximity window) of the gQRS peak location can be identified and the IQRS peak with the most positive amplitude in the subset or the IQRS peak that is closest to the corresponding gQRS peak can be classified as a normal positive peak. The parameter X may be 10-20 msec and preferably 10 msec, for example.

For each negative gQRS peak, the subset of negative IQRS peaks found within ±Y msec (which may be considered to be a proximity window) of the gQRS peak location can be identified and the IQRS peak with the most negative amplitude (in other words with the least amplitude) or the IQRS peak that is closest to the corresponding gQRS peak can be classified as a normal negative peak. The parameter Y may be 10-20 msec and preferably 10 msec, for example. In other embodiments, the parameters X and Y may have different values.

The remaining unclassified positive IQRS peaks can be classified as positive abnormal peaks and the remaining unclassified negative IQRS peaks can be classified as negative abnormal peaks. A QRSp score can then be determined based on the abnormal positive and abnormal negative IQRS peaks such as counting the total number of positive abnormal and negative abnormal IQRS peaks, for example.

The process of detecting abnormal peaks for a recording lead may be repeated for a set of consecutive short 10-50 beat ECG data windows that are incremented by a single beat from the first to the last of all of the 100-500 beats of ECG data to obtain a set of QRSpW scores. ECG data windows with a QRSpW score that occurs in fewer than N % of all windows, such as 5% for example, may be considered spurious and can be excluded from the subsequent QRSpL score calculations. The QRSpL score for each ECG lead may then be determined as the maximum, median or the mean QRSpW score across all 10-50 beat non-spurious data windows of that ECG lead (which are the same size as the data window used for the IQRS). For example, where there are 100 windows the QRSp for each ECG lead may be determined as the greatest or maximum QRSp value found in at least 5 of the 100 individual 10-beat windows.

In a similar manner, the QRSpL score may be independently determined for all remaining ECG leads. The likelihood of a patient responding to CRT treatment can be determined from the QRSpF score, which may be the maximum, median or mean QRSpL scores from some or all of the ECG recording leads. As described herein below, in some embodiments the maximum QRSpL score may be used as the QRSpF used to identify CRT candidates. For example, the maximum QRSpL score may be used in a statistical classification model and/or in a likelihood measure using a CRT threshold of 7 peaks.

In alternative embodiments, the likelihood of CRT response for a given patient may be determined using quantitative or qualitative likelihood measures that incorporate the QRSp score. For example, a qualitative or quantitative likelihood measure may incorporate the QRSp score into a statistical classification model to determine whether the patient is likely to respond to CRT. Examples of statistical classification models that may be used include, but are not limited to, logistic regression models, neural networks, Bayesian networks, or decision trees.

In some embodiments, a likelihood model may include QRSp scores and one or more additional relevant clinical variables (such as age, gender, etiology of cardiomyopathy, history of atrial fibrillation, left ventricular ejection fraction (LVEF), presence of left bundle branch block (LBBB) and QRS duration (QRSd) for example) from patients with heart failure who respond to CRT and patients with heart failure who do not respond to CRT. For example, multivariable logistic regression modelling may be used (see the Prospective Study described herein including Table 3) to determine a QRSp score odds ratio that adjusts for the effect of other CRT response predictor variables. In some embodiments, a patient's QRSp score in conjunction with the QRSp score odds ratio may then be used to provide a quantitative assessment of the likelihood of CRT response. For example, when the QRSp score odds ratio is 1.54 and a patient has a QRSp score of 7, they are considered 13.3 times more likely to respond to CRT than a patient with a QRSp score of 1. Alternatively, the likelihood of CRT response may be determined by inputting the patient's QRSp score and one or more other relevant clinical variables into a likelihood model to obtain a probability of CRT response for that patient. For example, a patient with a QRSp score of 10, a QRSd>150 ms and no history of AF may be considered to have a 0.88 probability of CRT response in a logistic regression model where the constant is −5.22 and the coefficients for the aforementioned variables (QRSp score, QRSd>150 ms, and no history of AF) are 0.43, 1.15 and 1.74, respectively.

In some embodiments described herein, the likelihood of CRT response may be determined quantitatively, e.g. as a probability, odds ratio etc. In other embodiments, the likelihood of CRT response may be determined as a qualitative indicator (e.g. Yes it is likely/No it is not likely). For example, when the CRT threshold is 7, a patient with a QRSp Max score of 10 may be classified as likely to respond, whereas a patient with a QRSp Max score of 3 may be classified as unlikely to respond. As another example, a decision tree may be used to determine a patient's likelihood of response. A patient's QRSp score can be used as a junction in one or more paths through the decision tree. The decision tree may include decision points based on a patient's specific QRSp and other clinical criteria to ultimately reach a final likelihood response of, for example, "Yes this patient is likely to respond to CRT" or "No this patient isn't likely to respond to CRT".

Referring now to FIG. 3A, shown therein is an Illustration of the abnormal QRS detection method applied to precordial ECG lead V5 of an ischemic cardiomyopathy (ICM) patient with heart failure. In the example shown in FIGS. 3A and 3B, for a 10 beat window, normal and abnormal QRS peaks were classified by comparing two different filtered versions of the QRS complex: (1) a smoothed global QRS average (gQRS) and (2) a non-smoothed local QRS average (lQRS). The gQRS was generated by applying a 15-point bidirectional moving average filter to the ECG and then signal averaging all 100 filtered QRS complexes. This produced a smoothed QRS complex with low frequency contours that portrays the major components of the depolarizing wavefront. Thus, all local maxima and minima in the gQRS are considered to be normal QRS peaks. In contrast, the lQRS was generated by signal averaging 10 consecutive QRS complexes within the 10-beat window without applying the additional moving average filter that was used to construct the gQRS. Since the lQRS is not smoothed like the gQRS, it not only contains the major components of the depolarizing wavefront but also retains minor perturbations that may relate to more localized conduction abnormalities. Accordingly, the local maxima and minima in the lQRS include both normal and abnormal QRS peaks. As illustrated in FIGS. 3A-3B, for a 10-beat window, the peaks on the lQRS corresponding, within 10 ms, to those on the gQRS were classified as normal, while those not corresponding to gQRS peaks were considered abnormal.

As shown in FIG. 3A, five positive (shown by circles) and 5 negative (shown by squares) abnormal QRS peaks are identified on the local QRS (lQRS) (shown by a solid line) after identifying 3 normal peaks (shown by diamonds) using the smoothed global QRS (gQRS) (shown by a dashed line). The number of positive and negative abnormal peaks may be summed to produce a QRSpW score of 10 for a single 10-50 beat data window from lead V5. FIG. 3B is a magnified view of FIG. 3A, which illustrates an example of normal QRS peak classification. A negative peak is identified on the smoothed gQRS (at the position labelled 'x'). The most negative peak on the lQRS within a certain time window, such as but not limited to ±10-20 msec, of the gQRS peak may be classified as normal.

Referring again to FIG. 2A, at act 108, a patient's responsiveness to CRT may be determined from the patient's QRSpF score, derived from analysis of all ECG leads. This may be performed by the CRT candidate assessment module 40 using a variety of different techniques.

A statistical model may be used to assess whether the patient is likely to respond to CRT. For example, the likelihood of response may be determined as a quantitative estimate of response associated with the QRSp score for the patient based on a multivariable regression model. Such a model may include QRSp scores from patients with heart failure who respond to CRT and patients with heart failure who do not respond to CRT. Such a model may also include additional clinical variables from both patients with heart failure who respond to CRT and patients with heart failure who do not respond to CRT, such as age, gender, etiology of cardiomyopathy, history of atrial fibrillation, left ventricular ejection fraction (LVEF), presence of left bundle branch block (LBBB) and QRS duration (QRSd) for example. This may be done using a multivariable regression model (see the Prospective Study described herein including Table 3) to determine a QRSp score odds ratio that adjusts for the effect of other CRT response predictor variables. A patient's QRSp score in conjunction with the QRSp score odds ratio may then be used to quantify the patient's likelihood of responding to CRT. Alternatively, the likelihood of CRT response may be determined by inputting the patient's QRSp score and other relevant clinical variables into a statistical model to obtain a probability of CRT response for that patient.

In alternative embodiments, a CRT threshold may be used to determine a patient's likelihood of responding to CRT. For example, a CRT threshold may be defined as a threshold number of abnormal peaks indicative of a patient being responsive to CRT. By comparing the patient's QRSpF score to the CRT threshold, the CRT candidate assessment module 40 can determine whether the patient is likely to respond to CRT and thus may be a candidate to undergo CRT.

Depending on the specific method used to determine the patient's QRSpF score, the CRT threshold may vary. For example, where the maximum QRSp value is used to define a patient's QRSpF score the CRT threshold may be defined as at least 5 abnormal QRS peaks. Thus, if a patient has 5 or more abnormal QRS peaks, the patient may be identified as a potential candidate for CRT. In some cases, the CRT threshold may be defined as at least seven (7) abnormal QRS peaks. Thus, if a patient has 7 or more abnormal QRS peaks, the patient may be identified as a potential candidate for CRT. As explained further below, the inventors have found that a CRT threshold of 7 abnormal peaks (when the QRSpF is determined as the maximum QRSpL) has the same sensitivity and greater specificity than QRSd at predicting patient responsiveness to CRT. Alternative CRT thresholds may also be selected, for instance where the QRSpF is determined based on the mean or median QRSpL.

In some cases, additional ECG metrics may be used in determining whether a patient is a candidate for CRT. For instance, the inventors have found that a combination of QRSd above a CRT threshold (e.g. 150 msec) and a QRSp above a CRT threshold (e.g. 7 where the maximum QRSpL is used as the QRSpF) can provide a further indication that a patient is likely to be responsive to CRT. Additional or different clinical variables may also be used in conjunction with a CRT threshold to determine the likelihood of a patient responding to CRT.

At act 110, an indication of abnormal QRSp and/or whether the patient is likely to respond to CRT (e.g. if the patient is a candidate for CRT) may be provided by displaying this information on the display 16 and/or saving this information in one of the databases 42. In some cases, a hardcopy report with this information may also be generated. Also, there may be some embodiments where this information is sent over the network to a physician or caregiver for the patient.

In some embodiments described herein, the likelihood of CRT response may be displayed quantitatively, e.g. as a probability of response, odds ratio etc. In other embodiments, the likelihood of CRT response may be determined as a qualitative indicator (e.g. Yes it is likely/No it is not likely).

In response to the indication shown at act 110, the patient may undergo cardiac resynchronization therapy. For instance, if the display 16 indicates that the patient is a good candidate for CRT (i.e. likely to respond to CRT) then the therapeutic decision can be made to perform CRT on the patient.

In some embodiments, act 112 may involve subsequent ECG data being obtained from the patient. The subsequent ECG data may be obtained in the same manner as at act 102 described above. Following CRT, the patient may undergo various tests to evaluate whether the CRT treatment has been effective.

The subsequent ECG data may be used to evaluate the performance of the CRT treatment. For instance, the subsequent ECG data may be analyzed to detect abnormal QRS peaks and to determine a subsequent QRSp score as described herein above. The subsequent QRSp score detected in the subsequent ECG data can be compared to the QRSp score prior to CRT treatment to evaluate changes in the electrical substrate for the patient.

Optionally, at act 114 an indication of the change in QRSp score (i.e. the difference in abnormal QRS peaks identified) may be provided by displaying this information on the display 16 and/or saving this information in one of the databases 42. In some cases, a hardcopy report with this information may also be generated. Also, there may be some embodiments where this information is sent over the network to a physician or caregiver for the patient. The inventors have found that patients responsive to CRT treatment tend to have a lower QRSp score at an interval of time following CRT—thus a reduced subsequent QRSp score can indicate a successful treatment. However, an increase in the subsequent QRSp score may indicate that the patient has not responded to the CRT treatment.

Long-term change in QRSp alone may provide a prognostic marker for mechanical recovery after CRT. Thus, the change in abnormal QRS peaks shown at act 114 can provide a quantifiable evaluation of the success of CRT for patients. This may provide clinicians with a simple evaluation tool to facilitate subsequent therapeutic decisions for a patient, such as altering the patient's medication or considering alternative surgical interventions.

Prospective Study

Forty-seven consecutive patients with ischemic or non-ischemic dilated cardiomyopathy undergoing CRT-defibrillator implantation (either de novo or upgrade from single or dual chamber ICD), according to current heart failure management guidelines were enrolled in a prospective study. Patients in complete heart block were excluded. Prior to consideration of CRT, all patients had an LV ejection fraction (EF)≤35%, a native QRS duration 20 ms, and had received optimal medical therapy for at least 3 months.

According to standard implantation procedures, all patients had a high voltage right ventricular (RV) lead placed in the RV apex and an LV lead placed in a postero-lateral or lateral tributary of the coronary sinus. Septal and apical LV stimulation were avoided where feasible. All but three patients with persistent atrial fibrillation (AF) underwent transvenous implantation of an atrial lead. Permanent CRT programming of AV delay, LV to RV delay and the LV stimulation vector was optimized for each patient as per the discretion of the treating electrophysiologist based on a combination of factors that included intrinsic PR interval, paced QRS morphology and QRSd after CRT.

A baseline ECG in native QRS rhythm was collected from all patients within the first 3 months of CRT and a follow-up study of native QRS rhythm was performed in 38 patients after 6 months of CRT. At each study, the skin was carefully prepared before recording high-resolution 12-lead ECGs for 3 minutes using a digital 12-lead Holter monitor (CardioMem CM 3000-12BT, Getemed Inc., Teltow, Germany) at a 1024 Hz sampling rate (0.05-120 Hz analogue bandwidth, ±6 mV voltage range, 12-bit digital resolution, 2.9 µV least significant bit). To minimize ECG noise, patients were required to lie still in the supine position with their hands at their sides for the duration of the recording.

Intrinsic QRSd was measured as the difference between the earliest QRS onset and the latest QRS offset on the baseline digital 12-lead ECG. The presence of intrinsic fQRS was assessed according to published criteria from a paper print out of the digital ECG using standard 12-lead ECG technical specifications (25 mm/s, 10 mm/mV, 0.01-150 Hz bandpass filter) (see Das et al., 2008).

Intrinsic QRSp was automatically quantified for each precordial lead (V1-V6) using software developed in MATLAB (Version 2012b, Mathworks, USA) that implemented the automated QRSp methods described herein above and in Applicant's PCT Publication No. WO2016/183683 (see also Suszko et al., 2015; Das et al., 2017). The precordial leads were used for analysis because each provides an independent unipolar recording. The QRSp for each lead (i.e. QRSpL) represented the total number of abnormal QRS deflections that deviated from a smoothed QRS template of that lead as described above.

Prior to QRSp detection, each lead was pre-processed to reduce noise and exclude irregular beats (e.g. noisy, paced, fused or ectopic beats). The first 100 consecutive, non-excluded QRS complexes in the 3-minute recording were used to quantify QRSp. For each lead, QRSp was assessed in consecutive 10-beat windows incremented by a single beat from the first to the last of the 100 QRS complexes. In each 10-beat window, abnormal QRS peaks were distinguished from normal QRS peaks by comparing two different filtered versions of the QRS complex: (1) a smoothed moving average filtered 100-beat global QRS average (gQRS) and (2) a non-smoothed 10-beat local QRS average (lQRS). The smoothed gQRS complex contains the major components of the depolarizing wavefront and all of its local maxima and minima are considered to be normal QRS peaks. However, the non-smoothed lQRS retains minor perturbations that may relate to more localized conduction abnormalities in addition to the major components of the depolarizing wavefront. Thus, peaks detected on the lQRS that are not present on the gQRS are considered to be abnormal as illustrated in FIGS. 3A and 3B. The QRSp for a 10-beat window was calculated as the total number of abnormal peaks identified in that window.

The QRSp for each precordial lead (V1p-V6p) was computed as the greatest or maximum QRSp value found in at least 5 of the 90 individual 10-beat windows. The QRSp Max and QRSp Mean were calculated for each patient as the maximum and mean of the six precordial lead QRSp values, respectively. Noise was assessed for each lead by computing the average ST segment root mean square noise value (RMS-ST) of all 100 beats.

Response to CRT was evaluated functionally based on echocardiographic-derived LVEF in all patients. Two-dimensional echocardiography was performed according to standard clinical procedures (see Lang et al., 2015) within 3 months prior to CRT and more than 6 months post-CRT. LVEF was calculated from the apical 2- and 4-chamber views using the biplane Simpson's method (see Schiller et al., 1989). Final interpretation was conducted by an echocardiographer blinded to the patient's clinical and ECG characteristics. CRT response was defined as an absolute increase in LVEF of greater than 5% between pre- and post-CRT assessments (see Cintron et al., 1993; Bleeker et al., 2006; Rickard et al., 2017).

In the results given herein, continuous variables are presented as mean±standard deviation or median and interquartile range (25th-75th percentiles) where appropriate. The Student's t test or the Mann-Whitney U-test were used for unpaired comparison between CRT responders and non-responders. Categorical variables are presented as frequency or percentage and were compared by the $\chi^2$ or Fisher's exact test. Amongst responder and non-responder groups, the paired t-test was used to compare continuous variables and McNemar's test was used to compare categorical variables between baseline and follow-up. One-way analysis of variance was used to compare variables between the patients divided into 4 groups based on combined optimal QRSp and QRSd cut-points. Correlations were assessed using Pearson's correlation coefficient.

Univariable and multivariable logistic regression analysis was used to assess the predictive value of clinical variables and QRSp Max for CRT response (see e.g. Table 3 below). Amongst the various methods of determining QRSp as described herein above, QRSp Max was identified as being significantly different between responders and non-responders and provided an aggregate evaluation of abnormal QRS peaks across all the precordial leads. The multivariable model included predictors with a univariable significance level of $P<0.1$ as well as QRSd due to its known associations with CRT response. Regression results are presented as the odds ratio and 95% confidence interval (OR [95% CI]). Accordingly, QRSp Max may preferably be used in the methods for detecting candidates responsive to CRT described herein, although QRSp Mean or QRSp Median may also be used in some embodiments.

Receiver operating characteristic (ROC) curves were constructed for QRSp and QRSd as predictors of CRT response. For QRSp, the optimal cut-point was assessed using Youden's index and the point closest to (0,1), while for QRSd, the conventionally accepted cut-point of 150 ms was used. The area under the paired ROC curves was compared between QRSp and QRSd using the DeLong test. Sensitivity and specificity were compared between QRSp and QRSd cut-points using NcNemar's test, while positive and negative predictive value were compared using a weighted generalized score statistic (see Kosinski et al., 2013).

All statistical analyses were performed using MATLAB (version 8.0, MathWorks, USA) or SPSS (version 20.0, SPSS Inc., USA). A two-sided $P<0.05$ was considered statistically significant, except when multiple comparisons were made amongst the family of QRSp variables (V1p, V2p, V3p, V4p, V5p, V6p, QRSp Max and QRSp Mean), in which cases a Bonferroni-corrected significance level of $P<0.00625$ was used to control for potential experiment-wise error.

Results

Patient characteristics and CRT parameters at the time of implant respectively are shown in Tables 1 and 2 below.

TABLE 1

Patient baseline characteristics

| | Total Sample (N = 47) | CRT Non-Responder (N = 19) | CRT Responder (N = 28) | P |
|---|---|---|---|---|
| Age, years | 62 ± 14 | 58 ± 16 | 64 ± 11 | 0.11 |
| Male, n (%) | 30 (64) | 12 (63) | 18 (64) | 1.00 |
| LVEF, % | 23 ± 7 | 23 ± 8 | 23 ± 7 | 0.93 |
| Cardiomyopathy, n (%) | | | | 1.00 |
| Ischemic | 16 (34) | 6 (32) | 10 (36) | |
| Non-Ischemic | 31 (66) | 13 (68) | 18 (64) | |
| NYHA Class, n (%) | | | | 0.34 |
| I* | 1 (2) | 1 (5) | 0 (0) | |
| II | 18 (38) | 5 (26) | 13 (46) | |
| III | 25 (53) | 12 (63) | 13 (46) | |
| IV | 3 (6) | 1 (5) | 2 (7) | |
| History of AF | 8 (17) | 6 (32) | 2 (7) | 0.047 |
| Creatinine (μmol/L) | 110 ± 68 | 114 ± 55 | 108 ± 75 | 0.76 |
| eGFR (ml/min) | 66 ± 22 | 62 ± 23 | 69 ± 22 | 0.30 |
| Medications | | | | |
| β-blocker, n (%) | 46 (98) | 19 (100) | 27 (96) | 1.00 |
| ACE Inhibitor/ARB, n (%) | 46 (98) | 18 (95) | 28 (100) | 0.40 |
| Diuretic, n (%) | 42 (89) | 18 (95) | 24 (86) | 0.64 |
| Digoxin, n (%) | 14 (30) | 8 (42) | 6 (21) | 0.20 |
| Amiodarone, n (%) | 10 (21) | 7 (37) | 3 (11) | 0.07 |
| Heart Rate, bpm | 69 ± 17 | 69 ± 19 | 70 ± 15 | 0.88 |
| Native QRS Morphology, n (%) | | | | 0.67 |
| LBBB | 41 (87) | 16 (84) | 25 (89) | |
| RBBB/IVCD | 6 (13) | 3 (16) | 3 (11) | |
| QRSd, ms | 173 ± 32 | 164 ± 30 | 179 ± 32 | 0.11 |
| QRSd ≥150 ms, n (%) | 38 (81) | 13 (68) | 25 (89) | 0.13 |
| fQRS, n (%) | 25 (53) | 8 (42) | 17 (61) | 0.25 |
| QRSp | | | | |
| V1p | 2.8 ± 2.9 | 3.1 ± 2.7 | 2.6 ± 3.1 | 0.574 |
| V2p | 2.1 ± 2.4 | 2.2 ± 2.3 | 2 ± 2.5 | 0.733 |
| V3p | 2.6 ± 3.5 | 1.7 ± 1.6 | 3.1 ± 4.3 | 0.132 |
| V4p | 4 ± 3.5 | 2.8 ± 2.1 | 4.7 ± 4 | 0.045 |
| V5p | 6.2 ± 3.8 | 4.9 ± 2.4 | 7 ± 4.4 | 0.046 |
| V6p | 5.4 ± 3.7 | 3.6 ± 2.4 | 6.7 ± 3.9 | 0.003† |
| QRSp Max | 7.8 ± 3.4 | 5.9 ± 2.2 | 9.1 ± 3.5 | 0.001† |
| QRSp Mean | 3.6 ± 2.1 | 2.9 ± 1.2 | 4 ± 2.5 | 0.085 |

In table 1, the following acronyms are used:
ACE, angiotensin converting enzyme;
AF, atrial fibrillation;
ARB, angiotensin receptor blocker;
CRT, cardiac resynchronization therapy;
fQRS, fragmented QRS;
IVCD, intraventricular conduction block;
LBBB, left bundle branch block;
LVEF, left ventricular ejection fraction;
OR, odds ratio;
QRSd, QRS duration;
QRSp, QRS peaks;
QRSp Max, maximum of precordial lead QRSp values;
QRSp Mean, mean of precordial lead QRSp values;
RBBB, right bundle branch block;
V1p-V6p, QRSp measured in leads V1 through V6
*NYHA class I patient with LVEF <35%, QRSd >120 ms and bradycardia-indication for pacing.
†QRSp variables below Bonferroni corrected significance level (p < 0.00625).

TABLE 2

| CRT Parameters | | | | |
|---|---|---|---|---|
| | Total Sample (N = 47) | CRT Non-Responder (N = 19) | CRT Responder (N = 28) | P |
| LV Circumferential Lead Position, n (%) | | | | 0.17 |
| Lateral | 10 (21) | 6 (32) | 4 (14) | |
| Posterolateral | 32 (68) | 10 (53) | 22 (79) | |
| Septal | 5 (11) | 3 (16) | 2 (7) | |
| LV Apico-Basal Lead Position, n (%) | | | | 0.29 |
| Basal | 14 (30) | 7 (37) | 7 (25) | |
| Mid | 32 (68) | 11 (58) | 21 (75) | |
| Apical | 1 (2) | 1 (5) | 0 (0) | |
| LV Pacing Configuration, n (%) | | | | 0.77 |
| Bipolar | 25 (53) | 11 (58) | 14 (50) | |
| Extended Bipolar | 22 (47) | 8 (42) | 14 (50) | |
| Sensed AV Delay, ms | 112 ± 18 | 111 ± 14 | 113 ± 20 | 0.78 |
| Paced AV Delay, ms | 152 ± 24 | 158 ± 19 | 148 ± 25 | 0.22 |
| LV to RV Delay | 35 ± 14 | 32 ± 13 | 36 ± 15 | 0.38 |
| BiV Pacing, % | 96 ± 6 | 96 ± 6 | 97 ± 7 | 0.61 |

In Table 2, the following acronyms are used: AV, atrioventricular; BiV, biventricular; CRT, cardiac resynchronization therapy; LV, left ventricular; RV, right ventricular.

All patients had both pre-CRT and post-CRT echocardiograms performed, with LV functional response to CRT observed in 28 (60%) patients. Median follow-up time for the post-CRT echocardiogram was 11.3 (7.4-14.7) months and was similar between responders and non-responders (11.7 (7.1-15.4) vs. 11.0 (7.5-13.8) months, p=0.60). The percentage of biventricular pacing at follow-up was 96±6% and did not differ between response groups (96±6 vs. 97±7%, p=0.61). The LVEF increased in responders (23.3±6.7 to 38.0±9.7%, p<0.001) but did not change in non-responders (23.4±8.2 to 24.2±7.9%, p=0.42). Fewer responders had a history of atrial fibrillation (AF) than non-responders (7 vs. 32%, p=0.047), while all other clinical and CRT parameters were similar between responders and non-responders.

Figures 4A, 4B:
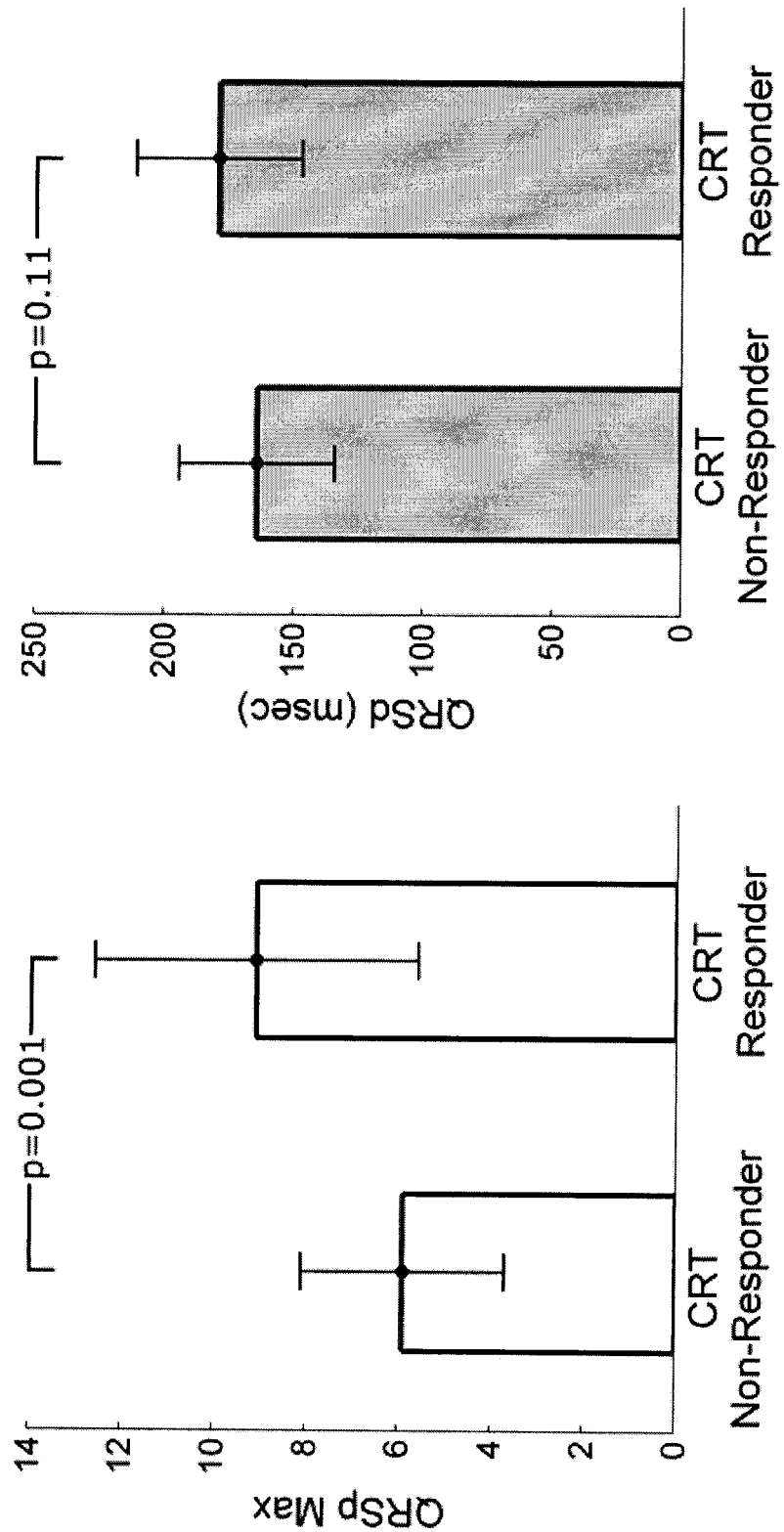
FIG. 4A shows an example plot of the average maximum number of abnormal QRS peaks in patients responsive to cardiac resynchronization therapy and in patients not responsive to cardiac resynchronization therapy.
FIG. 4B shows an example plot of average QRS duration in patients responsive to cardiac resynchronization therapy and in patients non-responsive to cardiac resynchronization therapy.

The baseline ECG study was conducted at a median 1.8 (1.3-2.4) months post-CRT and occurred at similar times in responders and non-responders (1.8 (1.3-2.4) vs. 1.8 (1.3-2.3) months, p=1.00). FIGS. 4A-4B illustrate bar graph plots showing the differences in QRSp Max and QRSd between CRT responders and non-responders. As presented in Table 1 above, baseline V6p (6.7±3.9 vs. 3.6±2.4, p=0.003) and QRSp Max (see FIG. 4A; 9.1±3.5 vs. 5.9±2.2, p=0.001) were greater in responders compared to non-responders.

There was also a trend toward greater V4p, V5p and QRSp Mean in responders (p<0.1). However, there was no difference in baseline QRSd (see FIG. 4B; 179±32 vs. 164±30 ms, p=0.11) or the proportion of patients with QRSd 150 ms (89 vs. 68%, p=0.13) between responders and non-responders. The prevalence of fQRS was similar between responders and non-responders (61 vs. 42%, p=0.25).

Figure 4C:
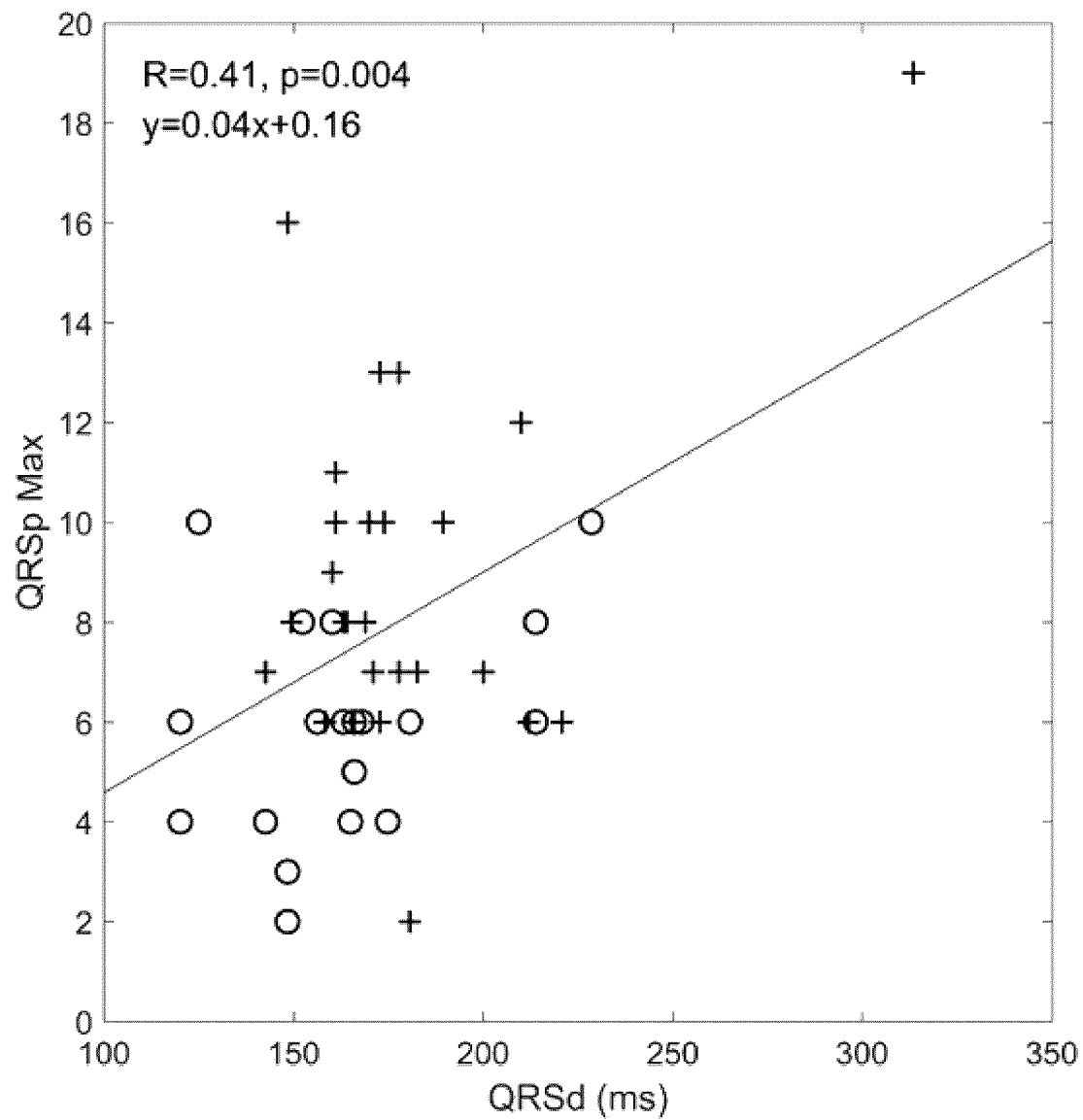
FIG. 4C shows an example plot of the correlation between the maximum number of abnormal QRS peaks and the QRS duration.

FIG. 4C is a scatter plot illustrating correlation between the baseline QRSp Max and QRSd for all 47 CRT patients. The 28 patients who were CRT responders are illustrated with crosses, while the 19 patients who were CRT non-responders are illustrated with circles. As illustrated in FIG. 4C, baseline QRSp Max and QRSd were only weakly positively correlated (r=0.41, p=0.004). There was no difference in QRSp Max between patients with and without fQRS (8.4±3.6 vs. 7.1±3.1, p=0.18), LBBB (7.6 vs. 9.2, p=0.30) or AF (6.5 vs. 8.1, p=0.23).

No correlation was observed between the QRSp and average RMS-ST noise value of each precordial lead (V1: r=0.10, p=0.52; V2: r=−0.10, p=0.52; V3: r=0.00, p=0.99; V4: r=−0.15, p=0.33; V5: r=0.00, p=1.00; V6: r=0.09, p=0.55), indicating that noise did not significantly contribute to the QRSp signal. There was also no difference in the precordial lead RMS-ST noise values between responders and non-responders (V1: 1.2±0.5 vs. 1.0±0.4 μV, p=0.13; V2: 1.1±0.4 vs. 0.9±0.3 μV, p=0.15; V3: 1.1±0.3 vs. 0.9±0.3 μV, p=0.09; V4: 1.1±0.3 vs. 1.0±0.3 μV, p=0.18; V5: 1.1±0.2 vs. 0.9±0.3 μV, p=0.13; V6: 1.0±0.2 vs. 0.9±0.3 μV, p=0.07).

Univariable and multivariable logistic regressions models for the prediction of CRT response are presented in Table 3.

TABLE 3

| Logistic regression analysis for prediction of CRT response | | | | | | |
|---|---|---|---|---|---|---|
| | Univariable Analysis | | Multivariable Model 1* | | Multivariable Model 2† | |
| | OR (95% CI) | P | OR (95% CI) | P | OR (95% CI) | P |
| Follow-up Time, mos | 1.02 (0.95-1.10) | 0.52 | — | — | — | — |
| Male | 1.05 (0.31-3.53) | 0.94 | — | — | — | — |
| Non-Ischemic CM | 0.83 (0.24-2.87) | 0.77 | — | — | — | — |
| History of AF | 0.17 (0.03-0.94) | 0.04 | 0.15 (0.02-1.34) | 0.09 | 0.18 (0.02-1.49) | 0.11 |
| LVEF (per 5%) | 0.98 (0.66-1.48) | 0.94 | — | — | — | — |
| LBBB | 1.56 (0.28-8.72) | 0.61 | — | — | — | — |
| QRSd ≥ 150 ms | 3.85 (0.83-17.9) | 0.09 | — | — | 3.15 (0.41-24.4) | 0.27 |
| QRSd (per 10 ms) | 1.23 (0.95-1.58) | 0.12 | 1.20 (0.87-1.65) | 0.27 | — | — |
| fQRS | 2.12 (0.65-6.95) | 0.21 | — | — | — | — |
| QRSp Max (per unit) | 1.58 (1.15-2.16) | 0.005 | 1.55 (1.11-2.16) | 0.01 | 1.54 (1.11-2.14) | 0.01 |

In table 3, the following acronyms are used: AF, atrial fibrillation; CI, confidence interval; CM, cardiomyopathy; fQRS, fragmented QRS; LBBB, left bundle branch block; LVEF, left ventricular ejection fraction; OR, odds ratio; QRSd, QRS duration; QRSp Max, maximum of precordial lead QRS peaks values
*C-Statistic = 0.84
†C-Statistic = 0.82

Univariable analysis revealed QRSp Max (OR [95% CI]: 1.58 (1.15-2.16), p=0.005), QRSd 150 ms (3.85 [0.83-17.9], p=0.09), and history of AF (0.17 (0.03-0.94), p=0.04) to be predictors of response to CRT. Multivariable analysis of the univariable predictors revealed QRSp Max to be the only independent predictor of CRT response in a model including QRSd as a continuous variable (OR [95% CI]: 1.55 [1.11-2.16], p=0.01; c-statistic=0.84) and another including QRSd≥150 ms as a dichotomous variable (1.54 [1.11-2.14], p=0.01; c-statistic=0.82).

Figure 5B:
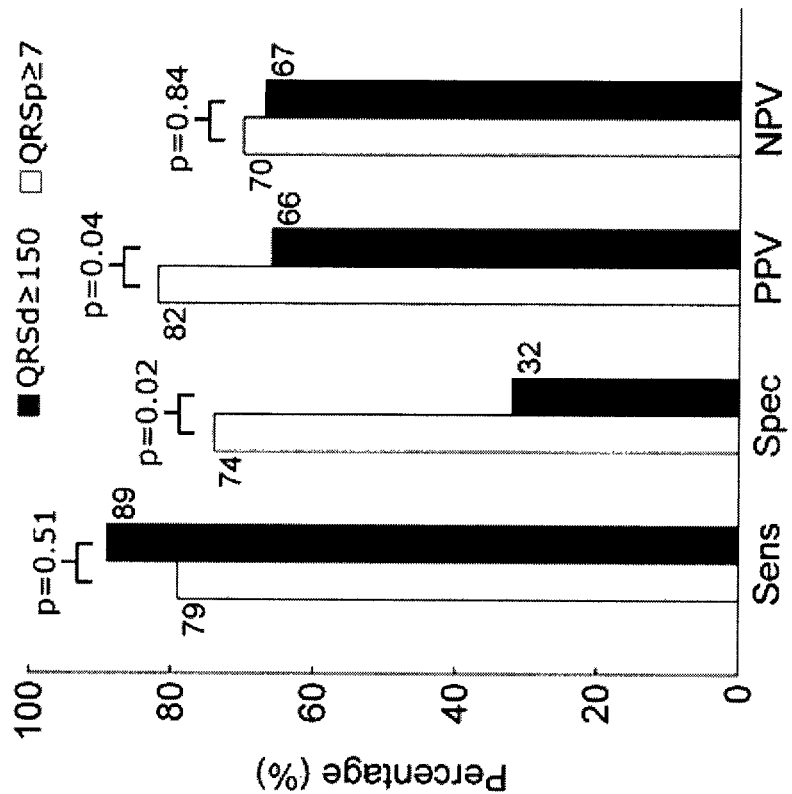
FIGS. 5A-5B show example plots of performance characteristics of using the maximum number of abnormal QRS peaks and the QRS duration as a predictor of responsiveness to cardiac resynchronization therapy.
Figure 5A:
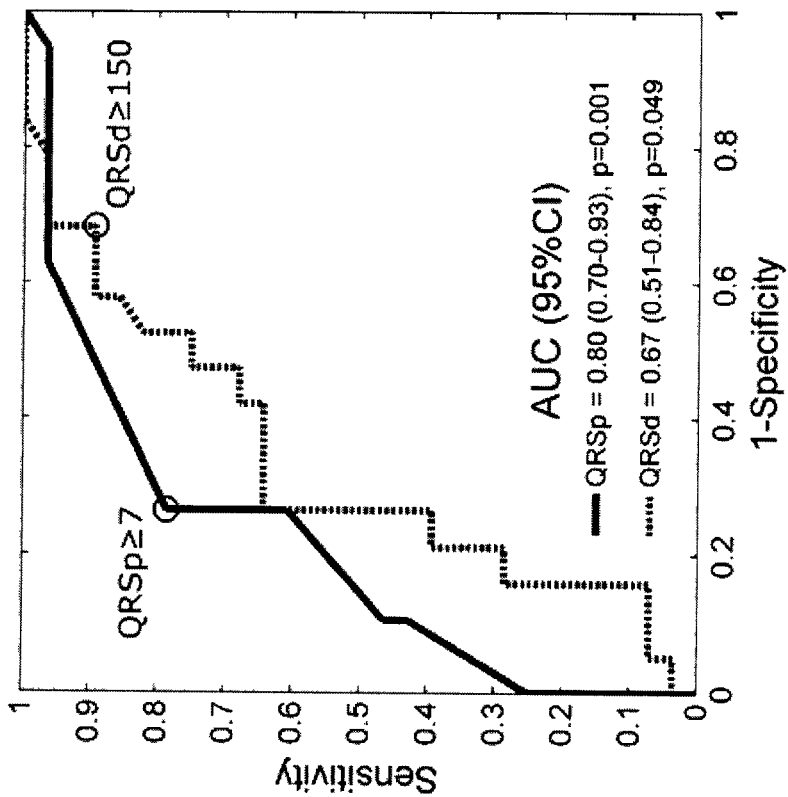

Since pre-implant QRSd is an established marker of CRT response, ROC analysis was used to evaluate the performance characteristics of QRSp Max compared to QRSd (see FIGS. 5A & 5B). FIG. 5A illustrates an ROC curve for QRSp Max (shown by the solid line) and an ROC curve for QRSd (shown by the dashed line) as a predictor of CRT response. Circles highlight the sensitivity and 1-specificity obtained by using a QRSp Max cut-point ≥7 and a QRSd cut-point≥150 ms. FIG. 5B illustrates bar graphs comparing the prognostic performance of the QRSp Max and QRSd cut-points for identifying CRT responders. It should be noted that the term cut-point is interchangeable with the word threshold.

Although the area under the ROC curve for identifying CRT responders was greater for QRSp Max (area under curve [95% confidence interval]: 0.80 [0.70-0.93], p=0.001) than for QRSd (0.67 [0.51-0.84], p=0.049), the difference between them was not statistically significant (p=0.21). For comparison with the conventional QRSd cut-point of ≥150 ms used to improve CRT, a QRSp Max cut-point of was selected as it was both the point closest to (0,1) on the ROC curve and the optimal cut-point defined by Youden's index for identifying CRT responders.

Using these cut-points, QRSp Max achieved similar sensitivity (79 vs. 89%, p=0.51) and negative predictive value (70 vs. 67%, p=0.84), but greater specificity (74 vs. 32%, p=0.02) and positive predictive value (82 vs. 66%, p=0.04) than QRSd 150 ms. The probability of CRT response was greater in patients with QRSp Max than in those with <7 (82% [22 of 27] vs. 30% [6 of 20], p=0.001; FIG. 5C), but similar in patients with QRSd 150 ms compared with those with <150 ms (66% [25 of 38] vs. 33% [3 of 9], p=0.13; FIG. 5D). FIG. 5C shows a bar graph comparing CRT responder rates between patients stratified by the optimal QRSp Max cut-point of while FIG. 5D shows CRT responder rates between patients stratified by the conventional QRSd cut-point of ≥150 ms. FIG. 5E shows CRT responder rates between patients stratified by the combination of both these cutpoints. While nearly all patients with both QRS≥150 ms and QRSp Max ≥7 responded to CRT, there were no responders amongst patients with both a QRS<150 ms and QRSp Max<7. AUC=area under the curve. 95% CI=95% confidence interval. PPV=positive predictive value. NPV=negative predictive value.

As shown in Table 4, there was no difference in clinical characteristics between patients with a QRSp ≥Max and <7.

TABLE 4

Baseline clinical characteristics in patients with QRSp <7 and ≥7

| | Total Sample (N = 47) | QRSp <7 (N = 20) | QRSp ≥7 (N = 27) | P |
|---|---|---|---|---|
| Age, years | 62 ± 14 | 60 ± 17 | 63 ± 11 | 0.56 |
| Male, n (%) | 30 (64) | 12 (60) | 18 (67) | 0.76 |
| LVEF, % | 23 ± 7 | 23 ± 8 | 24 ± 7 | 0.64 |

TABLE 4-continued

Baseline clinical characteristics in patients with QRSp <7 and ≥7

| | Total Sample (N = 47) | QRSp <7 (N = 20) | QRSp ≥7 (N = 27) | P |
|---|---|---|---|---|
| Cardiomyopathy, n (%) | | | | 0.12 |
| Ischemic | 16 (34) | 4 (20) | 12 (44) | |
| Non-Ischemic | 31 (66) | 16 (80) | 15 (56) | |
| NYHA Class, n (%) | | | | 0.67 |
| I† | 1 (2) | 1 (5) | 0 (0) | |
| II | 18 (38) | 8 (40) | 10 (37) | |
| III | 25 (53) | 10 (50) | 15 (56) | |
| IV | 3 (6) | 1 (5) | 2 (7) | |
| History of AF | 8 (17) | 4 (20) | 4 (15) | 0.71 |
| Creatinine (μmol/L) | 110 ± 68 | 118 ± 92 | 105 ± 43 | 0.56 |
| eGFR (ml/min) | 66 ± 22 | 67 ± 23 | 66 ± 22 | 0.82 |
| Medications | | | | |
| β-blocker, n (%) | 46 (98) | 20 (100) | 26 (96) | 1.00 |
| ACE Inhibitor/ARB, n (%) | 46 (98) | 20 (100) | 26 (96) | 1.00 |
| Diuretic, n (%) | 42 (89) | 17 (85) | 25 (93) | 0.64 |
| Digoxin, n (%) | 14 (30) | 6 (30) | 8 (30) | 1.00 |
| Amiodarone, n (%) | 10 (21) | 5 (25) | 5 (19) | 0.72 |
| Heart Rate, bpm | 69 ± 17 | 72 ± 19 | 67 ± 15 | 0.39 |
| Native QRS Morphology, n (%) | | | | 0.22 |
| LBBB | 41 (87) | 19 (95) | 22 (82) | |
| RBBB/IVCD | 6 (13) | 1 (5) | 5 (19) | |
| QRSd, ms | 173 ± 32 | 167 ± 27 | 177 ± 35 | 0.28 |
| QRSd ≥150 ms, n (%) | 38 (81) | 15 (75) | 23 (85) | 0.47 |
| fQRS, n (%) | 25 (53) | 9 (45) | 16 (59) | 0.39 |

ACE, angiotensin converting enzyme;
AF, atrial fibrillation;
ARB, angiotensin receptor blocker;
CRT, cardiac resynchronization therapy;
fQRS, fragmented QRS;
IVCD, intraventricular conduction block;
LBBB, left bundle branch block;
LVEF, left ventricular ejection fraction;
QRSd, QRS duration;
QRSp, QRS peaks As illustrated in FIG. 5E, the probability of CRT response was greatest in patients with QRSd≥150 ms and QRSp Max≥7 (83% [19 of 23]), followed by QRSd <150 ms and QRSp Max≥7 (75% [3 of 4]), QRSd ≥150 ms and QRSp Max <7 (40% [6 of 15]) and QRSd <150 ms and QRSp Max <7 (0% [0 of 5]) (p=0.002). These four categories also tracked structural remodeling, as the absolute LVEF improvement (ΔLVEF) was most pronounced in patients with QRSd ≥150 ms and QRSp Max≥7 (Δ12.2±8.9%), followed by QRSd <150 ms and QRSp Max≥7 (Δ9.6±8.8%), QRSd ≥150 ms and QRSp Max <7 (Δ7.3±8.8%) and QRSd <150 ms and QRSp Max <7 (Δ−1.0±4.7) (p=0.02). Table 5 summarizes additional patient and ECG characteristics of these 4 categories.

TABLE 5

LVEF, QRSd and QRSp characteristics in patients stratified by QRSd ≥150 ms and QRSp ≥7

| | QRSd <150 ms & QRSp Max <7 (N = 5) | QRSd ≥150 ms & QRSp Max <7 (N = 15) | QRSd <150 ms & QRSp Max ≥7 (N = 4) | QRSd ≥150 ms & QRSp Max ≥7 (N = 23) | P |
|---|---|---|---|---|---|
| Responders, n (%) | 0 (0) | 6 (40) | 3 (75) | 19 (83) | 0.002 |
| Baseline LVEF, % | 30 ± 9 | 20 ± 5 | 28 ± 6 | 23 ± 7 | 0.02 |
| Follow-up LVEF, % | 29 ± 11 | 28 ± 10 | 38 ± 9 | 35 ± 12 | 0.14 |

TABLE 5-continued

LVEF, QRSd and QRSp characteristics in patients stratified by QRSd ≥150 ms and QRSp ≥7

|  | QRSd <150 ms & QRSp Max <7 (N = 5) | QRSd ≥150 ms & QRSp Max <7 (N = 15) | QRSd <150 ms & QRSp Max ≥7 (N = 4) | QRSd ≥150 ms & QRSp Max ≥7 (N = 23) | P |
|---|---|---|---|---|---|
| Δ LVEF, % | −1.0 ± 4.7 | 7.3 ± 8.8 | 9.6 ± 8.8 | 12.1 ± 8.9 | 0.02 |
| Baseline QRSd, ms | 136 ± 15 | 178 ± 21 | 141 ± 11 | 184 ± 34 | 0.002 |
| Baseline QRSp |  |  |  |  |  |
| V1p | 1.6 ± 1.7 | 2.1 ± 2.0 | 4.5 ± 4.2 | 3.3 ± 3.3 | 0.31 |
| V2p | 1.2 ± 1.1 | 1.3 ± 1.5 | 1.3 ± 1.9 | 2.9 ± 2.9 | 0.16 |
| V3p | 1.2 ± 1.8 | 2.0 ± 2.0 | 0.5 ± 1.0 | 3.6 ± 4.5 | 0.22 |
| V4p | 1.6 ± 1.7 | 2.7 ± 1.8 | 3.0 ± 1.2 | 5.4 ± 4.2 | 0.03 |
| V5p | 2.2 ± 1.5 | 4.6 ± 1.7 | 9.5 ± 5.0 | 7.5 ± 4.0 | 0.002 |
| V6p | 2.6 ± 1.9 | 3.7 ± 2.0 | 5.5 ± 2.4 | 7.2 ± 4.2 | 0.007 |
| QRSp Max | 3.8 ± 1.5 | 5.4 ± 1.2 | 10.3 ± 4.0 | 9.8 ± 2.8 | <0.001 |
| QRSp Mean | 1.7 ± 0.5 | 2.6 ± 0.9 | 3.8 ± 0.5 | 4.6 ± 2.5 | 0.005 |

In table 4, the following acronyms are used:
LVEF, left ventricular ejection fraction;
QRSd, QRS duration;
QRSp, QRS peaks;
QRSp Max, maximum of precordial lead QRSp values;
QRSp Mean, mean of precordial lead QRSp values;
RBBB, right bundle branch block;
V1p-V6p, QRSp measured in leads V1 through V6

Figure 6B:
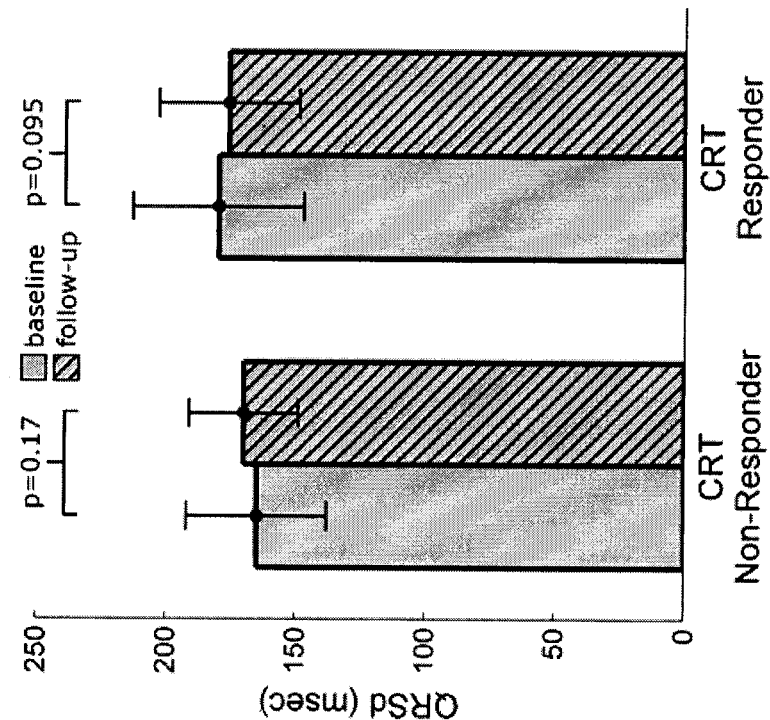
FIG. 6B shows an example plot of the change in QRS duration following CRT in patients responsive to cardiac resynchronization therapy and patient non-responsive to cardiac resynchronization therapy.
Figure 6A:
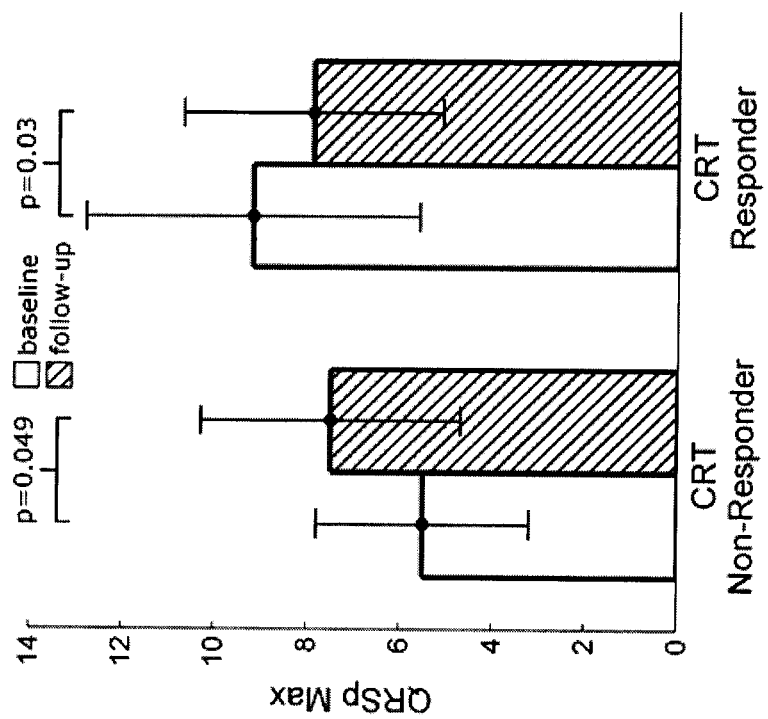
FIG. 6A shows an example plot of the change in number of abnormal QRS peaks following CRT in patients responsive to cardiac resynchronization therapy and patient non-responsive to cardiac resynchronization therapy.

Amongst the 38 patients with repeat ECG studies, the follow-up ECG was performed at a median 8.3 (7.4-11.9) months post-CRT with a trend toward being earlier in responders than non-responders (7.9 (6.7-10.6) vs. 11.6 (7.8-14.6), p=0.06). FIGS. 6A-6B illustrates changes in QRSp and QRSd from baseline to follow-up in CRT responders and non-responders. As shown in FIG. 6A, QRSp Max decreased in responders (9.2±3.6 vs. 7.9±2.8, p=0.03) but increased in non-responders (5.5±2.3 vs. 7.5±2.8, p=0.049). As shown in FIG. 6B, while there was a trend toward reduction of QRSd in responders (180±33 vs. 176±27, p=0.095), QRSd in non-responders remained similar (165±27 vs. 170±31, p=0.17). There was no change in the prevalence of fQRS amongst responders (59 vs. 81%, p=0.15) or non-responders (45 vs. 64%, p=0.50).

Figure 7A:
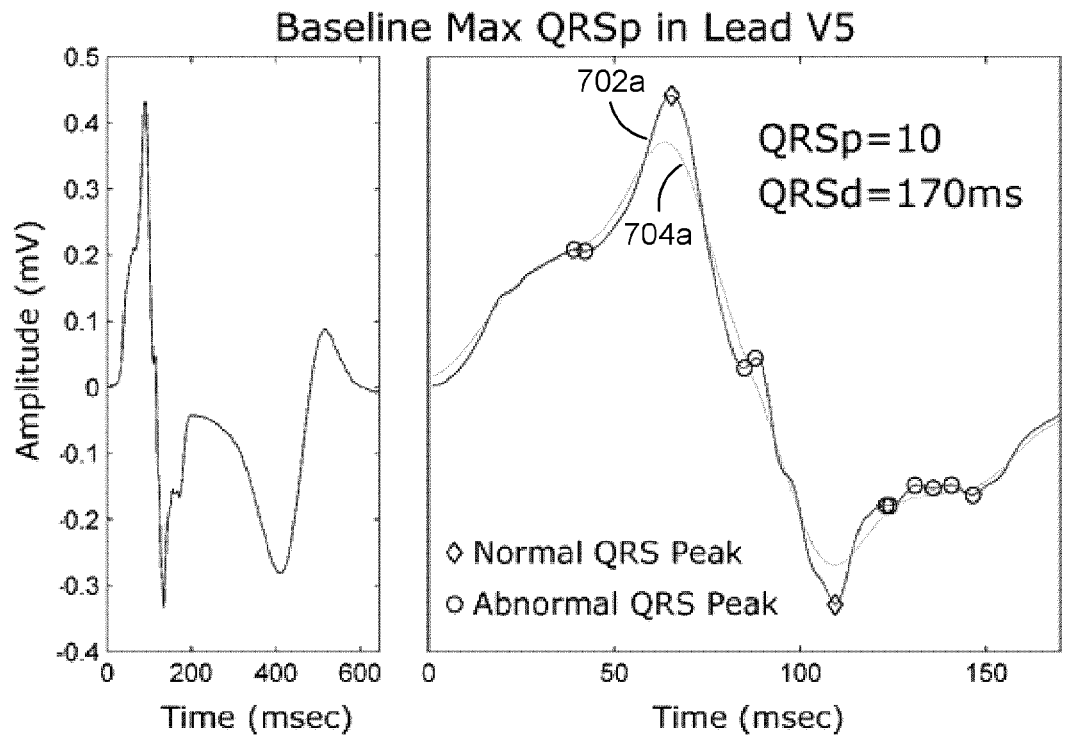
FIGS. 7A-7B show plots of the number of abnormal QRS peaks in baseline and follow-up testing for a patient responsive to CRT with a baseline QRS duration greater than 150 ms.
Figure 7B:
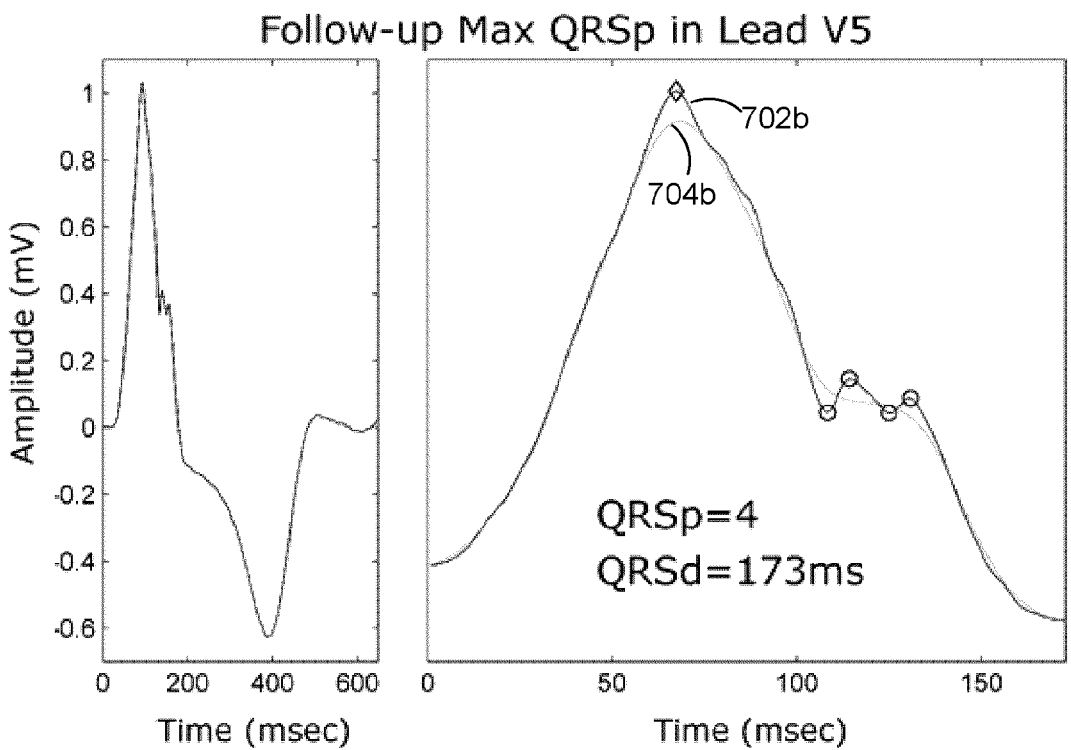
Figure 7C:
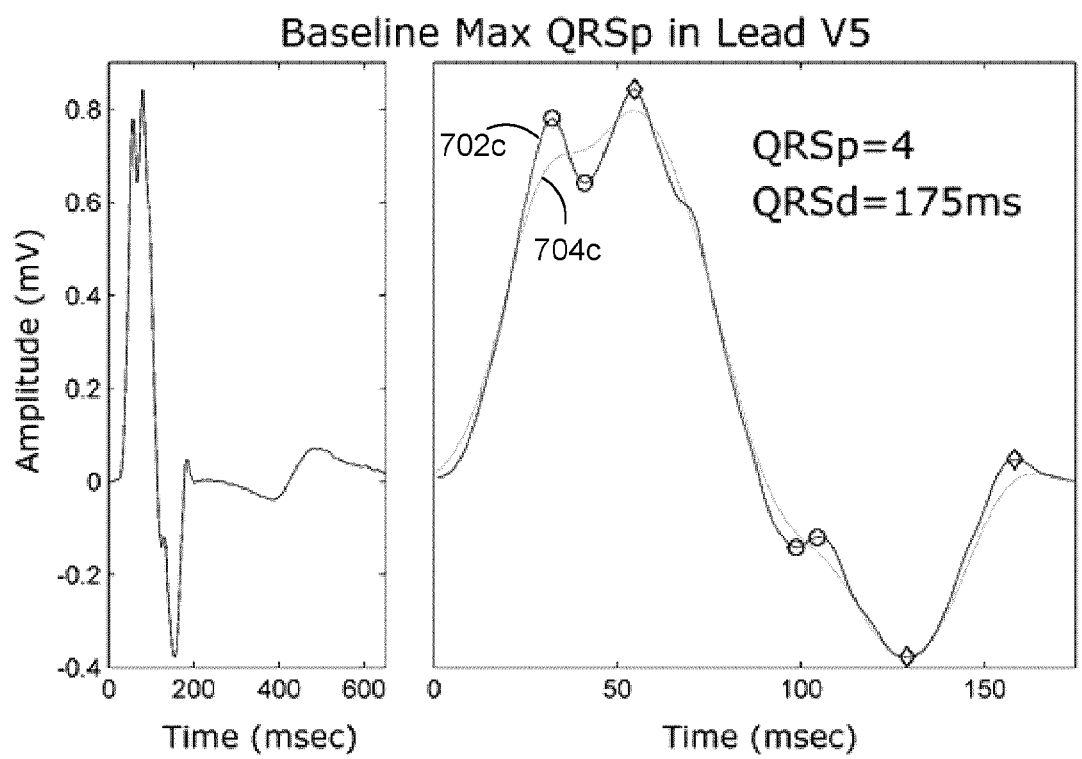
FIG. 7C-7D show plots of the number of abnormal QRS peaks in baseline and follow-up testing for a patient not responsive to CRT with a baseline QRS duration greater than 150 ms.
Figure 7D:
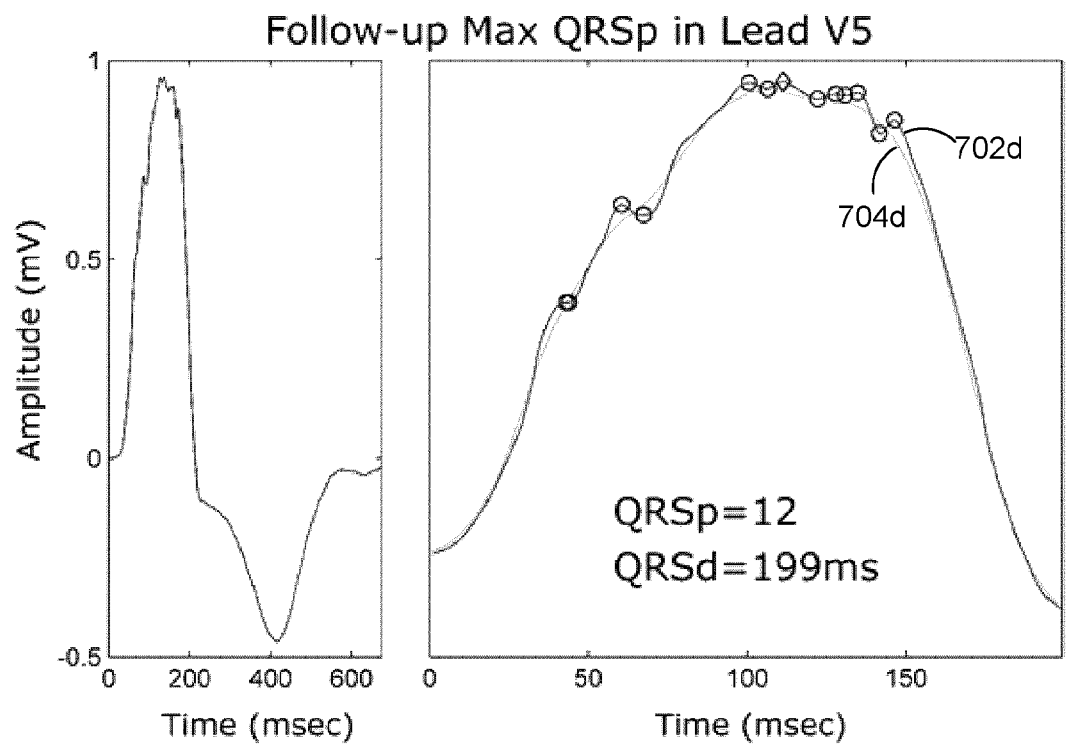
Figure 7E:
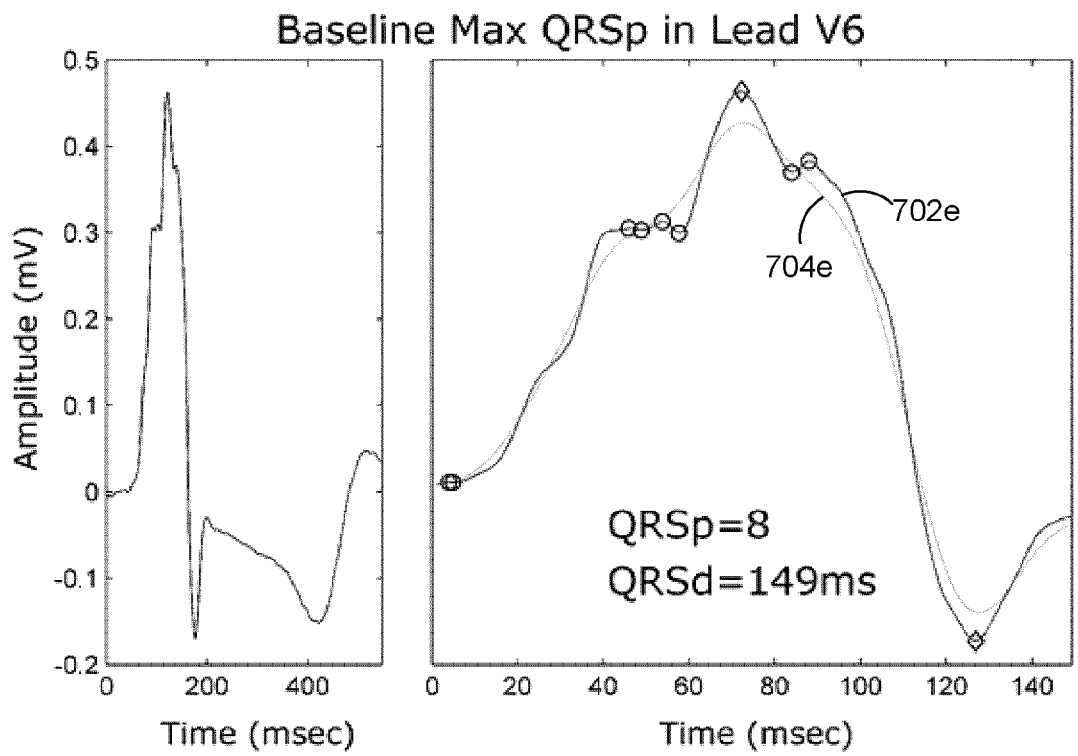
FIG. 7E-7F show plots of the number of abnormal QRS peaks in baseline and follow-up testing for a patient responsive to CRT with a baseline QRS duration less than 150 ms.
Figure 7F:
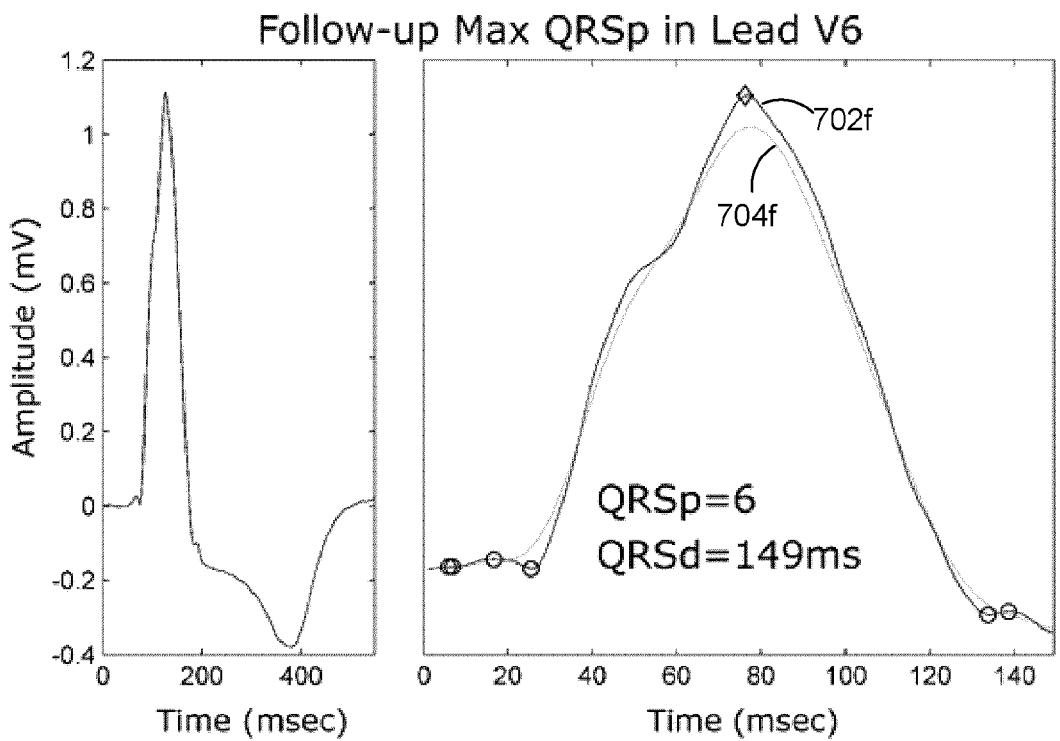
Figure 7G:
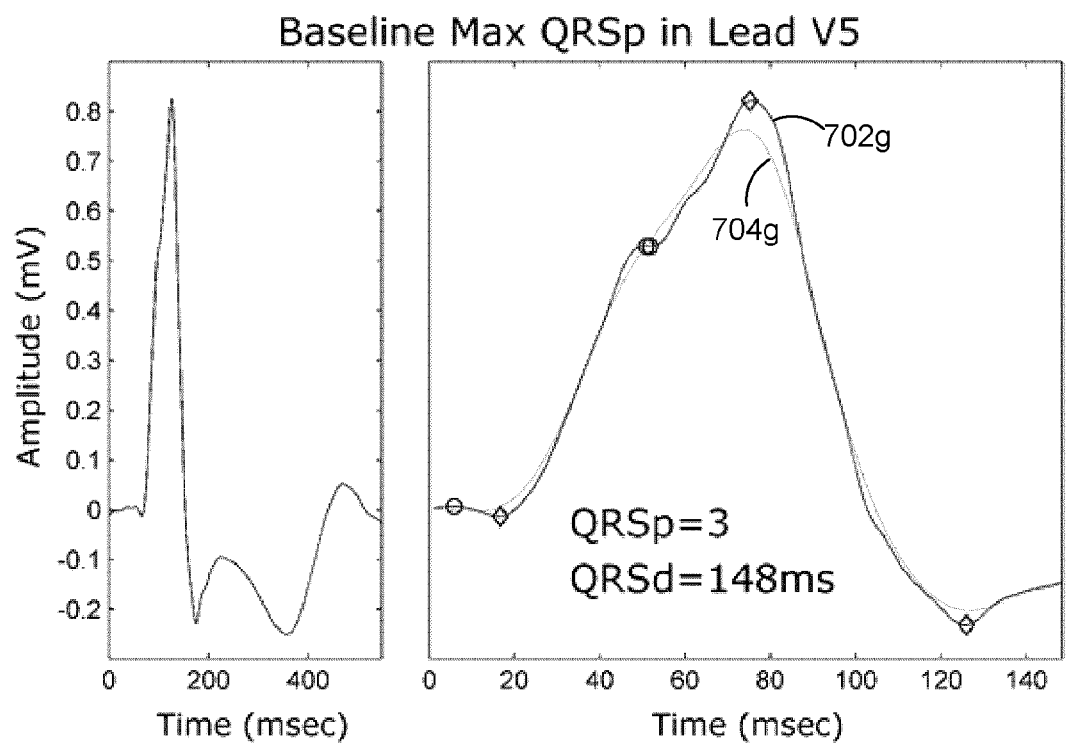
FIG. 7G-7H show plots of the number of abnormal QRS peaks in baseline and follow-up testing for a patient not responsive to CRT with a baseline QRS duration less than 150 ms.
Figure 7H:
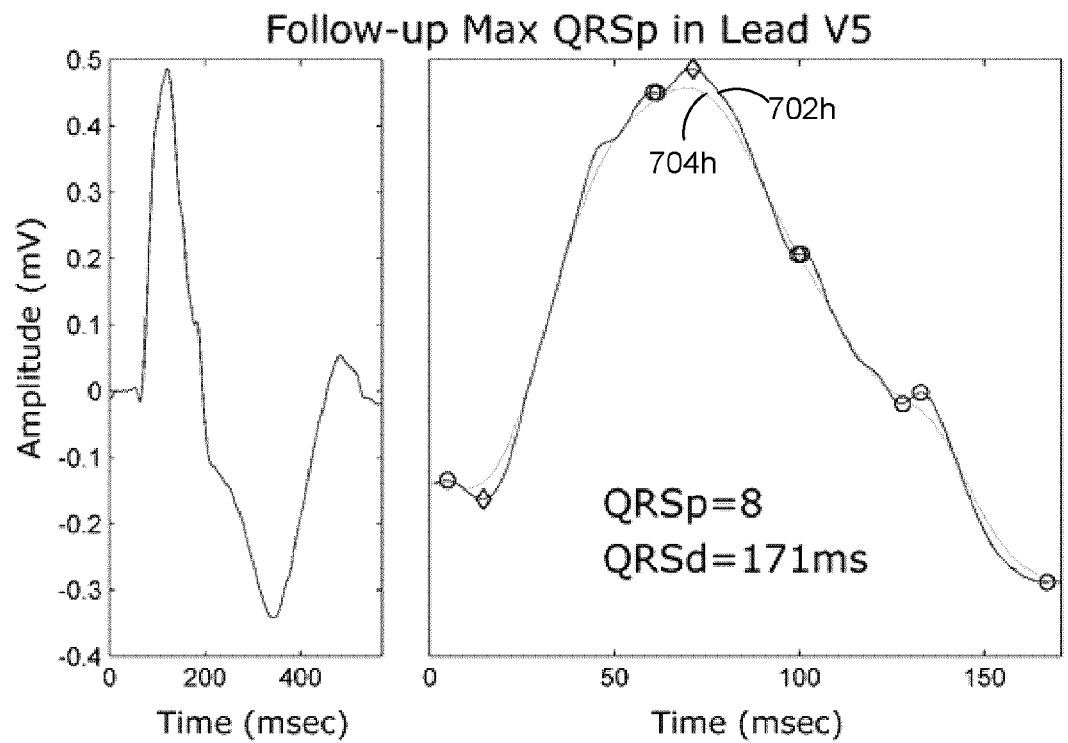

FIGS. 7A-7H illustrate QRS complexes with baseline QRSd above and below 150 ms in CRT responders and non-responders. The left-hand panels depict the 10-beat average complex including the QRS and T wave, while the right-hand panels depict the enlarged 10-beat QRS average with peak annotations. The black lines (702a-h) show the lQRS and the grey lines (704a-h) show the gQRS. Normal peaks are annotated with diamonds, and abnormal peaks are annotated with circles. FIGS. 7A-7B illustrate a CRT responder with QRSd above 150 ms and a baseline QRSp Max≥7 and FIGS. 7E-7F illustrate a CRT responder with QRSd below 150 ms and a baseline QRSp Max≥7. As shown in FIGS. 7B and 7F, the QRSp Max decreases in follow-up. FIGS. 7C-7D illustrate a patient who is not responsive to CRT with QRSd above 150 ms and a baseline QRSp Max<7 and FIGS. 7G-7H illustrate a patient who is not responsive to CRT with QRSd below 150 ms and a baseline QRSp Max<7. As shown in FIGS. 7D and 7H, the QRSp Max increases in follow-up. From baseline to follow-up, it was generally observed that the QRS complex became visually smoother in responders but more fragmented in non-responders as is seen in the representative examples of FIGS. 7A-7H.

The study results indicate that QRSp independently predicts functional CRT response in cardiomyopathy patients, unlike QRSd, LBBB or fQRS. In particular, a QRSp Max identifies CRT responders with greater accuracy than QRSd 150 ms or fQRS. Additionally, QRSp Max decreases in CRT responders while increasing in CRT non-responders, whereas QRSd and fQRS do not change irrespective of CRT response.

Electrical conduction delay in the LV causes dyssynchronous activation, which may respond to CRT. Currently, electrical dyssynchrony assessment for CRT eligibility is based solely on the QRSd 120 ms and LBBB morphology. While these contemporary criteria have high sensitivity, they lack specificity to predict CRT response. Moreover, in patients with QRSd<150 ms, there are limited data on markers of electrical dyssynchrony. Recognition of patients prior to device implantation who are likely to achieve benefit or are at a heightened risk of non-response to CRT has been challenging.

As shown above, QRSp Max independently predicts functional CRT response in cardiomyopathy patients after adjusting for QRSd, while LBBB and fQRS were not predictive. For each unit increase in QRSp Max, the odds of CRT response increases by 1.6 fold. QRSp Max≥7 identified CRT responders with similar sensitivity as QRSd, but with significantly greater specificity (74 vs. 32%) and positive predictive value (82 vs. 66%). Importantly, QRSp Max discriminated CRT responders from non-responders among patients with QRSd>150 ms as well as those with QRSd<150 ms. Patients with QRSd≥150 ms who also had QRSp of ≥7 had a >2-fold higher probability of attaining functional CRT response (83% vs. 40%) and a larger LVEF improvement compared to those with QRSp Max<7. In addition, although a minority of the study patients had QRSd<150 ms, QRSp Max<7 in this group predicted 100% non-response to CRT.

Electrical resynchronization of the ventricles with CRT is mediated by fusion of RV and LV propagating wavefronts, which reduces global activation time and mitigates conduction block. This may result in an acute narrowing in the paced QRSd and a reduction in paced fQRS prevalence compared to that in native QRS. With long-term CRT, there is evidence of reverse electrical remodeling amongst CRT responders. Narrowing of the native QRSd has been reported in both functional and clinical CRT responders (see Karaca et al., 2016; Sebag et al., 2012), while complete reversion of LBBB has been linked with super-response (see Dizon et al., 2004). In a prospective study of 85 CRT patients with LBBB, Sebag et al. reported a decrease in intrinsic QRSd from 168±20 ms pre-CRT to 149±31 ms at 1-year post-CRT, which was associated with a greater rate of LVEF improvement. In addition, Celikyurt et al. 2015 observed a reduction in the prevalence of native fQRS amongst CRT patients with LBBB who demonstrated a decrease in LV end systolic volume >15% at 6 months post-CRT. Electrical remodeling in CRT responders may arise from structural and molecular changes in the cardiac electric substrate. Besides restoration of the cardiomyocyte size and reduction in collagen fraction, there is improvement in kinetics of intracellular calcium cycling with up-regulation of sarcoplasmic reticulum calcium ATPase 2c and ryanodine receptor, and sodium-calcium exchanger levels in those with LVEF improvement post CRT (see Vanderheyden et al., 2008; Wang et al., 2017). No significant changes in molecular profile are observed in non-responders. In line with these data, the inventors found a significant reduction in QRSp in patients who had improvement in LVEF, but an increase in QRSp in non-responders. In contrast, changes in native QRSd were less evident in the study, although there was a trend toward a decrease in responders, but no change in non-responders. The study results also did not show any change in fQRS prevalence in CRT responders or non-responders. Therefore, a long-term change in QRSp alone may also provide a prognostic marker for mechanical recovery after CRT.

Fragmentation of the QRS complex on the standard 12-lead ECG reflects conduction delay and abnormal wavefront propagation caused by fibrotic infiltration and/or ventricular ion-current remodeling (see Das et al., 2009). A linkage between fQRS and myocardial scarring was originally described in patients with narrow QRS (<120 ms) but has since been extended to patients with wide QRS, paced QRS and premature ventricular beats. In this regard, native fQRS has been associated with major adverse events in patients with both ischemic and non-ischemic heart disease, with increased risk of ventricular arrhythmias and death.

Amongst the CRT population, paced fQRS has also been associated with future ventricular tachyarrhythmia events and sudden cardiac death in patients with non-ischemic cardiomyopathy. Paradoxically, in the same study and another that included both ischemic and non-ischemic cardiomyopathy, CRT patients with native fQRS had equivalent mortality risk compared to those without fQRS. Native fQRS has also been associated with echocardiographic-derived inter- and intra-ventricular dyssynchrony in two observational studies of 286 cumulative patients with non-ischemic cardiomyopathy and QRSd<120 ms. However, in those with a wider QRSd, mechanical dyssynchrony appears to be equally prevalent in patients with and without native fQRS. Only a few studies have evaluated the relation of native fQRS to functional CRT response and their results are conflicting. In a retrospective study of 232 CRT patients, Rickard et al demonstrated fQRS in 21% of the cohort and there was no difference in LVEF improvement or LV end diastolic volume reduction between those with and without fQRS. In a smaller prospective study of 53 patients of whom 31% manifested fQRS, the absence of fQRS was an independent predictor of functional CRT response (OR 1.55, p=0.028).

As shown above, QRSp provides an independent prediction of functional CRT response. Furthermore, a higher QRSp indicates that greater LVEF recovery is likely in both patients with QRSd<150 ms as well as those with QRSd 150 ms. On the other hand, fQRS was not found to be associated with functional CRT response. This discrepancy from the above-mentioned fQRS-based studies indicates that the quantitative evaluation of QRS fragmentation with QRSp provides a more specific measure of electrical dyssynchrony. No difference in QRSp was shown between patients with and without fQRS.

Embodiments described herein for automated quantification of abnormal QRS peaks (QRSp) from high-resolution ECGs can provide an independent predictor of CRT response in patients with cardiomyopathy. Additionally, a QRSp Max≥7 can identify CRT responders with similar sensitivity as QRSd, but with significantly greater specificity. For each additional unit of QRSp Max, the odds of CRT response increases by 1.6 fold providing an improved confidence that a patient is responsive to CRT. In addition, a long-term change in QRSp Max has been seen to track mechanical recovery in CRT responders.

While the applicant's teachings described herein are in conjunction with various embodiments for illustrative purposes, it is not intended that the applicant's teachings be limited to such embodiments. On the contrary, the applicant's teachings described and illustrated herein encompass various alternatives, modifications, and equivalents, without departing from the embodiments described herein, the general scope of which is defined in the appended claims.

REFERENCES

Auricchio A, Fantoni C, Regoli F, Carbucicchio C, Goette A, Geller C, Kloss M, Klein H. Characterization of left ventricular activation in patients with heart failure and left bundle-branch block. *Circulation.* 2004; 109:1133-1139.

Auricchio A, Lumens J, Prinzen F W. Does Cardiac Resynchronization Therapy Benefit Patients With Right Bundle Branch Block: Cardiac Resynchronization Therapy Has a Role in Patients With Right Bundle Branch Block. *Circ Arrhythm Electrophysiol.* 2014; 7:532-542.

Birnie D H, Ha A, Higginson L, Sidhu K, Green M, Philippon F, Thibault B, Wells G, Tang A. Impact of QRS morphology and duration on outcomes after cardiac resynchronization therapy: Results from the Resynchronization-Defibrillation for Ambulatory Heart Failure Trial (RAFT). *Circulation Heart Fail.* 2013; 6:1190-1198.

Bleeker G B, Bax J J, Fung J W, van der Wall E E, Zhang Q, Schalij M J, Chan J Y, Yu C M. Clinical versus echocardiographic parameters to assess response to cardiac resynchronization therapy. *Am J Cardiol.* 2006; 97:260-3.

Celikyurt U, Agacdiken A, Sahin T, Al N, Vural A, Ural D. Relationship between fragmented QRS and response to cardiac resynchronization therapy. *J Interv Card Electrophysiol.* 2012; 35:337-42.

Celikyurt U, Karauzum K, Sahin T, Agacdiken A, Vural A, Ural D. Association between resolution of fragmented QRS and response to cardiac resynchronization therapy. *Ann Noninvasive Electrocardiol.* 2015; 20:126-31.

Cintron G, Johnson G, Francis G, Cobb F, Cohn J N. Prognostic significance of serial changes in left ventricular ejection fraction in patients with congestive heart failure. The V-HeFT V A Cooperative Studies Group. *Circulation.* 1993; 87:VI17-23.

Das M K, Suradi H, Maskoun W, Michael M A, Shen C, Peng J, Dandamudi G, Mahenthiran J. Fragmented wide QRS on a 12-lead ECG: a sign of myocardial scar and poor prognosis. *Circ Arrhythm Electrophysiol.* 2008; 1:258-268.

Das M K, Zipes D P: Fragmented QRS: a predictor of mortality and sudden cardiac death. *Heart Rhythm.* 2009; 6:S8-14.

Das M K, Maskoun W, Shen C, Michael M A, Suradi H, Desai M, Subbarao R, Bhakta D. Fragmented QRS on twelve-lead electrocardiogram predicts arrhythmic events in patients with ischemic and nonischemic cardiomyopathy. *Heart Rhythm.* 2010; 7:74-80.

Das M, Suszko A M, Nayyar S, Viswanathan K, Spears D A, Tomlinson G, Pinter A, Crystal E, Dalvi R, Krishnan S, Chauhan V S. Automated Quantification of Low-Amplitude Abnormal QRS Peaks From High-Resolution ECG Recordings Predicts Arrhythmic Events in Patients With Cardiomyopathy. *Circ Arrhythm Electrophysiol.* 2017; 10:e004874.

Dizon J, Horn E, Neglia J, Medina N, Garan H. Loss of left bundle branch block following biventricular pacing therapy for heart failure: evidence for electrical remodeling? *J Interv Card Electrophysiol.* 2004; 10:47-50.

Flowers N C, Horan L G, Thomas J R, Tolleson W J. The anatomic basis for high-frequency components in the electrocardiogram. *Circulation.* 1969; 39:531-539.

Gold M R, Birgersdotter-Green U, Singh J P, Ellenbogen K A, Yu Y, Meyer T E, Seth M, Tchou P J. The relationship between ventricular electrical delay and left ventricular remodelling with cardiac resynchronization therapy. *Eur Heart J.* 2011; 32:2516-2524.

Hawkins N M, Petrie M C, MacDonald M R, Hogg K J, McMurray J J. Selecting patients for cardiac resynchronization therapy: electrical or mechanical dyssynchrony? *Eur Heart J.* 2006; 27:1270-1281.

Igarashi M, Tada H, Yamasaki H, Kuroki K, Ishizu T, Seo Y, Machino T, Murakoshi N, Sekiguchi Y, Noguchi Y, Nogami A, Aonuma K. Fragmented QRS Is a Novel Risk Factor for Ventricular Arrhythmic Events After Receiving Cardiac Resynchronization Therapy in Nonischemic Cardiomyopathy. *J Cardiovasc Electrophysiol.* 2017; 28:327-335.

Karaca O, Cakal B, Omaygenc M O, Gunes H M, Cakal S D, Kizilirmak F, Gokdeniz T, Barutcu I, Bortosun B, Kilicaslan F. Native Electrocardiographic QRS Duration after Cardiac Resynchronization Therapy: The Impact on Clinical Outcomes and Prognosis. *J Card Fail.* 2016; 22:772-80.

Khan F Z, Virdee M S, Palmer C R, Pugh P J, O'Halloran D, Elsik M, Read P A, Begley D, Fynn S P, Dutka D P. Targeted left ventricular lead placement to guide cardiac resynchronization therapy: the TARGET study: a randomized, controlled trial. *J Am Coll Cardiol.* 2012; 59:1509-1518.

Kosinski A S. A weighted generalized score statistic for comparison of predictive values of diagnostic tests. *Stat Med.* 2013; 32:964-77.

Lang R M, Badano L P, Mor-Avi V, Afilalo J, Armstrong A, Ernande L, Flachskampf F A, Foster E, Goldstein S A, Kuznetsova T, Lancellotti P, Muraru D, Picard M H, Rietzschel E R, Rudski L, Spencer K T, Tsang W, Voigt J U. Recommendations for cardiac chamber quantification by echocardiography in adults: an update from the American Society of Echocardiography and the European Association of Cardiovascular Imaging. *J Am Soc Echocardiogr.* 2015; 28:1-39.

Leyva F, Nisam S, Auricchio A. 20 years of cardiac resynchronization therapy. *J Am Coll Cardiol.* 2014; 64:1047-1058.

Rickard J, Zardkoohi O, Popovic Z, Verhaert D, Sraow D, Baranowski B, Martin D O, Grimm R A, Chung M K, Tchou P, Lindsay B A, Wilkoff B L. QRS fragmentation is not associated with poor response to cardiac resynchronization therapy. *Ann Noninvasive Electrocardiol.* 2011; 16:165-171.

Rickard J, Baranowski B, Grimm R A, Niebauer M, Varma N, Tang WHW, Wilkoff B L. Left Ventricular Size does not Modify the Effect of QRS Duration in Predicting Response to Cardiac Resynchronization Therapy. *Pacing Clin Electrophysiot* 2017; 40:482-487.

Russo A M, Stainback R F, Bailey S R, Epstein A E, Heidenreich P A, Jessup M, Kapa S, Kremers M S, Lindsay B D, Stevenson L W. ACCF/HRS/AHA/ASE/HFSA/SCAI/SCCT/SCMR 2013 appropriate use criteria for implantable cardioverter-defibrillators and cardiac resynchronization therapy: a report of the American College of Cardiology Foundation appropriate use criteria task force, Heart Rhythm Society, American Heart Association, American Society of Echocardiography, Heart Failure Society of America, Society for Cardiovascular Angiography and Interventions, Society of Cardiovascular Computed Tomography, and Society for Cardiovascular Magnetic Resonance. *J Am Coll Cardiol.* 2013; 61:1318-1368.

Schiller N B, Shah P M, Crawford M, DeMaria A, Devereux R, Feigenbaum H, Gutgesell H, Reichek N, Sahn D, Schnittger I. Recommendations for quantitation of the left ventricle by two-dimensional echocardiography. American Society of Echocardiography Committee on Standards, Subcommittee on Quantitation of Two-Dimensional Echocardiograms. *J Am Soc Echocardiogr.* 1989; 2:358-67.

Sebag F A, Martins R P, Defaye P, Hidden-Lucet F, Mabo P, Daubert J C, Leclercq C. Reverse electrical remodeling by cardiac resynchronization therapy: prevalence and clinical impact. *J Cardiovasc Electrophysiol.* 2012; 23:1219-27.

Sinha S K, Bhagat K, Asif M, Singh K, Sachan M, Mishra V, Afdaali N, Jha M J, Kumar A, Singh S, Sinha R, Khanra D, Thakur R, Varma C M, Krishna V, Pandey U. Fragmented QRS as a Marker of Electrical Dyssynchrony to Predict Inter-Ventricular Conduction Defect by Subsequent Echocardiographic Assessment in Symptomatic Patients of Non-Ischemic Dilated Cardiomyopathy. *Cardiology Res.* 2016; 7:140-145.

Suszko A M, Dalvi R, Das M, Chauhan V S. Quantifying abnormal QRS peaks using a novel time-domain peak detection algorithm: Application in patients with cardiomyopathy at risk of sudden death. 2015 *IEEE International Conference on Electro/Information Technology (EIT).* 2015; 020-024.

Tigen K, Karaahmet T, Gurel E, Cevik C, Nugent K, Pala S, Tanalp A C, Mutlu B, Basaran Y. The utility of fragmented QRS complexes to predict significant intraventricular dyssynchrony in nonischemic dilated cardiomyopathy patients with a narrow QRS interval. *Can J Cardiol.* 2009; 25:517-522.

Vanderheyden M, Mullens W, Delrue L, Goethals M, de Bruyne B, Wijns W, Geelen P, Verstreken S, Wellens F, Bartunek J. Myocardial gene expression in heart failure patients treated with cardiac resynchronization therapy responders versus nonresponders. *J Am Coll Cardiol.* 2008; 51:129-136.

Wang J, Gong X, Chen H, Qin S, Zhou N, Su Y, Ge J. Effect of Cardiac Resynchronization Therapy on Myocardial Fibrosis and Relevant Cytokines in a Canine Model With Experimental Heart Failure. *J Cardiovasc Electrophysiol.* 2017; 28:438-445.

The invention claimed is:

1. A computer implemented method of assessing the likelihood of response to cardiac resynchronization therapy (CRT) for a patient, the method comprising:
   receiving, by a processing unit, time-domain ECG data obtained from the patient;
   analyzing, by the processing unit, the time-domain ECG data to detect abnormal QRS peaks using a sliding window;
   determining, by the processing unit, a QRS peak (QRSp) score by quantifying the abnormal QRS peaks in the sliding window of the time-domain ECG data;
   determining, by the processing unit, a measure of likelihood of CRT response for the patient based on the QRSp score by inputting the QRSp score into a statistical classification model to obtain a probability of CRT response for that patient; and indicating that the patient is a candidate for CRT based on the measure of likelihood of CRT response,
   wherein the statistical classification model is generated using QRSp scores from patients with heart failure who do not respond to CRT and patients with heart failure who respond to CRT;
   wherein the measure of likelihood of CRT response is used to identify candidates likely to respond to CRT; and
   determining a treatment regimen for the patient in response to the indication that the patient is a candidate for CRT, wherein the treatment regime includes performing CRT on the patient.

2. The method of claim 1, wherein the method comprises acquiring the ECG data from the patient using a plurality of ECG recording leads.

3. The method of claim 2, wherein the act of analyzing the ECG data from a given ECG recording lead comprises:
   generating a local QRS (IQRS) signal from X beats of ECG data;
   generating a global QRS (gQRS) signal from Y beats of ECG data, where X and Y are integers and the X beats of ECG data are contained in the Y beats of ECG data; and
   comparing the IQRS signal with the gQRS signal to detect the abnormal QRS peaks in the IQRS signal.

4. The method of claim 3, wherein the IQRS signal is generated by applying time averaging to unfiltered X beats of preprocessed ECG data, and the gQRS signal is generated by filtering the Y beats of preprocessed ECG data using a smoothing filter and then applying time averaging to the filtered Y beats of ECG data, where the X beats of ECG data is a short data window and the Y beats of ECG data is a larger data window that is at least one order of magnitude larger than the short data window.

5. The method of claim 3, wherein the comparing comprises:
   identifying positive and negative peaks in the IQRS and gQRS signals;
   determining abnormal positive peaks in the IQRS signal by counting the number of positive peaks in the IQRS signal within ±M msec of each positive peak in the gQRS signal while excluding the nearest or greatest amplitude IQRS peak within ±M msec of each positive peak in the gQRS signal;
   determining abnormal negative peaks in the IQRS signal by counting the number of negative peaks in the IQRS signal within ±M msec of each negative peak in the gQRS signal while excluding the nearest or least amplitude IQRS peak within ±M msec of each negative peak in the gQRS signal; and
   determining the QRSp score as the total of the abnormal positive peaks and the abnormal negative peaks in the IQRS signal.

6. The method of claim 5, wherein the QRSp score for the patient is a mean, median or maximum of the QRSp scores for ECG data obtained from at least a portion of the ECG recording leads.

7. The method of claim 1, wherein the ECG data comprises several sets of ECG data obtained using different ECG leads and the QRSp score is determined for each set of ECG data.

8. The method of claim 1, wherein the ECG data comprises precordial ECG data obtained using precordial leads.

9. The method of claim 1, further comprising inputting at least one other clinical variable for the patient into the statistical classification model to obtain the probability of CRT response for that patient.

10. The method of claim 9, wherein the at least one other clinical variable includes age, gender, etiology of cardiomyopathy, history of atrial fibrillation, left ventricular ejection fraction (LVEF), presence of left bundle branch block (LBBB) and/or QRS duration (QRSd).

11. The method of claim 1, wherein the statistical classification model comprises one of a multivariable regression model, a decision tree model, a neural network model and a support vector machine model.

12. The method of claim 6, wherein the QRSp score is the maximum of the QRSp scores for ECG data obtained from the at least a portion of the ECG recording leads.

13. The method of claim 1, further comprising:
   receiving subsequent ECG data obtained from the patient following the performance of CRT on the patient;
   analyzing the subsequent ECG data to detect subsequent abnormal QRS peaks;
   comparing the number of subsequent abnormal QRS peaks to the number of abnormal QRS peaks; and
   providing an indication of a change in the number of abnormal QRS peaks based on the comparison.

14. The method of claim 13, further comprising modifying the patient's treatment regimen in response to the change in the number of abnormal QRS peaks.

15. A system for identifying the likelihood of CRT response for a patient to guide CRT candidate selection, wherein the system comprises:
   an input interface for receiving ECG data obtained from the patient;
   an output interface for providing a measure of likelihood of CRT response for the patient; and
   a processing unit coupled to the input and the output interfaces, the processing unit being configured to:
      analyze time-domain ECG data in the ECG data obtained from the patient to detect abnormal QRS peaks using a sliding window;
      determine a QRS peak (QRSp) score by quantifying the abnormal QRS peaks in the sliding window of the time-domain ECG data;
      determine a measure of likelihood of CRT response for the patient based on the QRSp score by inputting the QRSp score into a statistical classification model to obtain a probability of CRT response for that patient; and
      provide an indication that the patient is a candidate for CRT based on the measure of likelihood of CRT response, wherein the statistical classification model is generated using QRSp scores from patients with heart failure who do not respond to CRT and patients with heart failure who respond to CRT;

wherein the measure of likelihood of CRT response is used to identify candidates likely to respond to CRT; and wherein a treatment regimen for the patient is determined in response to the indication that the patient is a candidate for CRT, wherein the treatment regime includes performing CRT on the patient.

16. The system of claim 15, wherein the ECG data is acquired from the patient using a plurality of ECG recording leads and the processing unit is configured to analyze the ECG data to detect abnormal QRS peaks from a given ECG recording lead by: generating a local QRS (lQRS) signal from X beats of ECG data; generating a global QRS (gQRS) signal from Y beats of ECG data, where X and Y are integers and the X beats of ECG data are contained in the Y beats of ECG data; and comparing the lQRS signal with the gQRS signal to detect the abnormal QRS peaks in the lQRS signal.

17. The system of 16, wherein the processing unit is configured to compare the lQRS signal with the gQRS signal to detect the abnormal QRS peaks in the lQRS signal by: identifying positive and negative peaks in the lQRS and gQRS signals; determining abnormal positive peaks in the lQRS signal by counting the number of positive peaks in the lQRS signal within ±M msec of each positive peak in the gQRS signal while excluding the nearest or greatest amplitude lQRS peak within ±M msec of each positive peak in the gQRS signal; determining abnormal negative peaks in the lQRS signal by counting the number of negative peaks in the lQRS signal within ±M msec of each negative peak in the gQRS signal while excluding the nearest or least amplitude lQRS peak within ±M msec of each negative peak in the gQRS signal; and determining the QRSp score as the total of the abnormal positive peaks and the abnormal negative peaks in the lQRS signal.

18. A computer implemented method of assessing the likelihood of response to cardiac resynchronization therapy (CRT) for a patient, the method comprising:

receiving, by a processing unit, time-domain ECG data obtained from the patient;

analyzing, by the processing unit, the time-domain ECG data to detect abnormal QRS peaks using a sliding window;

determining, by the processing unit, a QRS peak (QRSp) score by quantifying the abnormal QRS peaks in the sliding window of the time-domain ECG data;

determining, by the processing unit, a measure of likelihood of CRT response for the patient based on the QRSp score;

assigning a CRT peak threshold based on a number of abnormal QRS peaks;

comparing the QRSp score to the CRT peak threshold; and indicating that the patient is a candidate for CRT if the QRSp score is greater than the CRT peak threshold, wherein the measure of likelihood of CRT response is used to identify candidates likely to respond to CRT; and a treatment regimen for the patient is determined in response to the indication that the patient is a candidate for CR, wherein the treatment regime includes performing CRT on the patient.

19. The method of claim 18, wherein the QRSp score for the patient is a mean, median or maximum of the QRSp scores for ECG data obtained from at least a portion of ECG recording leads.

20. The method of claim 19, wherein the QRSp score is the maximum of the QRSp scores; and the CRT peak threshold is at least 7.

* * * * *